US006224878B1

(12) United States Patent
Leung-Tack et al.

(10) Patent No.: US 6,224,878 B1
(45) Date of Patent: May 1, 2001

(54) MUTANTS AND VACCINES OF THE INFECTIOUS BOVINE RHINOTRACHEITIS VIRUS

(75) Inventors: Patricia Leung-Tack, Villeurbanne; Isabelle Christine Marie-Andrée Legastelois, Mornant; Jean-Christophe Francis Audonnet, Lyons; Michel Emile Albert Riviere, Ecully, all of (FR)

(73) Assignee: Merial, Lyons (FR)

( * ) Notice: Subject to any disclaimer, the term of this patent is extended or adjusted under 35 U.S.C. 154(b) by 0 days.

(21) Appl. No.: 08/924,345

(22) Filed: Sep. 4, 1997

Related U.S. Application Data

(63) Continuation of application No. 08/199,172, filed as application No. PCT/FR93/00642 on Jun. 25, 1992, now abandoned.

(30) Foreign Application Priority Data

Jun. 26, 1989 (FR) .............................................. 92 07930

(51) Int. Cl.[7] ........................ A61K 39/12; A61K 39/245; C12N 15/00; C12Q 1/70

(52) U.S. Cl. .................................... 424/199.1; 424/229.1; 424/813; 424/205.1; 435/320.1; 435/235.1; 435/69.3; 435/5; 536/23.72

(58) Field of Search ............................. 424/199.1, 205.1, 424/229.1, 813; 435/320.1, 235.1, 69.3, 5; 536/23.72

(56) References Cited

U.S. PATENT DOCUMENTS

| | | | | |
|---|---|---|---|---|
| 4,992,051 | * | 2/1991 | Kit et al. | 435/235.1 |
| 5,223,424 | * | 6/1993 | Cochran et al. | 435/236 |
| 5,585,264 | * | 12/1996 | Babiuk et al. | 435/240.2 |
| 5,789,177 | * | 8/1998 | Rijsewijk et al. | 435/71 |

FOREIGN PATENT DOCUMENTS

| | | | | |
|---|---|---|---|---|
| 0316658 | * | 5/1989 | (EP) | C12N/15/00 |
| 0663403 A1 | * | 7/1995 | (EP) | C07K/14/06 |
| 9221751 | * | 12/1992 | (WO) | C12N/15/00 |
| 9302104 | * | 2/1993 | (WO) | C07K/7/10 |

OTHER PUBLICATIONS

Leung–Tak et al. "The Complete DNA Sequence and the Genetic Organization of the Short Unique Region (Us) of the Bovine Herpesvirus Type 1(ST Strain)". Virology. vol. 199:409–421, 1994.* van Drunen Littel–van den Hurk, S. et al. 1990. Vaccine vol. 8 pp. 358–368.*

Simard, C. et al. 1990. Arch. Virol. vol. 110 pp. 63–75.*

Fehler, F. et al. 1992, J. Virol. vol. 66 pp. 831–839.*

Leung–Tak, P. et al. 1994. Virology vol. 199 pp. 409–421.* van Oirschot et al., "Development of an ELISA for detection of antibodies in glycoprotein I of Aujeszky's disease . . . ", Journal of Virological Methods, 22 (1988) pp. 191–206.

McGeoch, "Evolutionary relationships of virion glycoprotein genes in the S regions of alphaherpesvirus genomes", Journal of General Virology (1990), 71, pp. 2361–2367.

Mayfield et al., "Cloning and Cleavage Site Mapping of DNA from Bovine Herpesvirus I (Cooper Strain)", Journal of Virology, Jul. 1983, pp. 259–264.

Tikoo et al., "Molecular Cloning, Sequencing, and Expression of Functional Bovine Herpesvirus I Glycoprotein gIV in Transfected Bovine Cells", Journal of Virology, Oct. 1990, pp. 5132–5143.

Audonnet et al., "Equine herpesvirus type I unique short fragment encodes glycoproteins with homology to herpes simplex virus type 1 gD, gI and gE", Journal of General Virology (1990), 71, pp. 2969–2978.

Petrovskis et al., "Use of λgt11 to Isolate Gens for Two Pseudorabies Virus Glycoproteins with Homology to Herpes Simplex Virus and Varicella–Zoster Virus Glycoproteins", Journal of Virology, Oct. 1986, pp. 185–193.

Mayfield et al., "Cloning and Cleavage Site Mapping of DNA from Bovine Herpesvirus 1 (Cooper Strain)", Journal of Virology, Jul. 1983, pp. 259–264.

Neidhardt et al., "Herpes Simplex Virus Type 1 Glycoprotein E Is Not Indispensible for Viral Infectivity", Journal of Virology, Feb. 1987, pp. 600–603.

van Oirschot et al., "Marker vaccines, virus protein–specific antibody assays and the control of Aujeszky's disease", Veterinary Microbiology, 23 (1990), pp. 85–101.

McGeoch et al., "Sequence Determination and Genetic Content of the Short Unique Region in the Genome of Herpes Simplex Virus Type 1", J. Mol. Biol. (1985), 181, pp. 1–13.

*Primary Examiner*—Ali R. Salimi
(74) *Attorney, Agent, or Firm*—Larson & Taylor

(57) ABSTRACT

A recombinant virus is provided which is obtained from a BHV virus originally having the gI gene whose DNA sequence is delimited by nucleotides 172 and 1311 of SEQ ID NO:1 herein and which has been mutated by total or partial deletion and/or insertion in this region. By the mutation in this region, there is no longer any expression of the glycoprotein which has been mutated or rendered inactive, and thus animals vaccinated with these mutants do not develop antibodies against the glycoprotein and can be serologically distinguished from animals infected by field BHV-1 strains and other vaccinal strains currently used. A method of using the present recombinant virus is also provided which allows one to distinguish infected animals from vaccinated animals in a manner that has not previously been possible using presently available commercial vaccines. The invention is thus advantageous in that the mutant viruses obtained by the invention can be used as vectors for expression of various foreign genes so as to prepare useful vaccines against bovine and ruminant diseases.

1 Claim, 17 Drawing Sheets

OTHER PUBLICATIONS

Wirth et al., "Spatial and Temporal Distribution of Bovine Herpesvirus 1 Transcripts", Journal of Virology, Nov. 1989, pp. 4882–4889.

Declaration of Dr. M. Schwyzer, Jun. 23, 1997, Zurich (in EP 0 587 805).

Declaration of Dr. Nico Visser, Jun. 25, 1997, Boxmeer (in EP 0 587 805).

van Orischot et al., "6.2 Construction of a recombinant vector vaccine against bovine herpes virus (BHV) type 1 and bovine respiratory syncytial virus (BRSV) infections", pp. 122–127 (1990).

* cited by examiner

INFORMATION FOR SEQ ID NO.: 1

1) SEQUENCE CHARACTERISTICS:
   a) LENGTH: 4 190 BASE PAIRS
   b) TYPE: NUCLEOTIDES

2) STRANDEDNESS: DOUBLE STRAND

3) SEQUENCE TOPOLOGY: LINEAR

4) TYPE: GENOMIC DNA

5) HYPOTHETICAL SEQUENCE: NO

6) ANTISENSE: NO

7) ORIGINAL SOURCE OF THE MOLECULE:
   a) ORGANISM: TYPE 1 BOVINE HERPESVIRUS
   b) STRAIN: ST

8) EXPERIMENTAL SOURCE:
   a) GENOMIC LIBRARY

FIG. 2A

```
TTTGGCAACG TCAACTACAG CGCGCTGCCC GGGTGAGCGG CCTAGGCCCT CCCCCGACCG 60

CCCCCTTTGC TCCTAGCCCC CGGCTCCAGC CGAGCCGCGC GGGGCGGAGA TAAAGCGCCC 120

GCGTCGGCGA CTCAAGCCAT TGCCGCGACC TTGTCCTCCG GCGCGCTCGC G ATG CGG  177
                                                         Met Arg
                                                           1

TGC CTG TTG CTC TGG ATC GTG GTG CTG GCC GCG CGA GCC GCC CCC GCT   225
Cys Leu Leu Leu Trp Met Val Val Leu Ala Ala Arg Ala Ala Pro Ala
          5                  10                  15

CGC AGC CTT GTG TAT CGC GGC GAG GCA GTC GGC CTG GGC CCG GAG GGG   273
Arg Ser Leu Val Tyr Arg Gly Glu Ala Val Gly Leu Arg Ala Asp Gly
     20                  25                  30

CCC GTA GCG TTC GCT GTC CAC CCG ACC GAC GCA ACG CTC GCG CTG CGG   321
Pro Val Ala Phe Ala Val His Pro Thr Asp Ala Thr Leu Ala Leu Arg
 35                  40                  45                  50

GGC CGG CTG ATT TTC CTG GAA CAC CAG CTC CCG GCC GGG CGG CGC TAC   369
Gly Arg Leu Ile Phe Leu Glu His Gln Leu Pro Ala Gly Arg Arg Tyr
                 55                  60                  65
```

FIG. 2B

```
AAC GGG ACC GTC GAG CTG CTG CGC TAC CAC GCC GCG GGC GAC TGC TTC    417
Asn Gly Thr Val Glu Leu Leu Arg Tyr His Ala Ala Gly Asp Cys Phe
             70                  75                  80

GTT ATG CTG CAG ACG ACC GCG TTC GCC TCC TGC CCG CGC GTC GCG AAC    465
Val Met Leu Gln Thr Thr Ala Phe Ala Ser Cys Pro Arg Val Ala Asn
         85                  90                  95

AAC GCC TTT CGC TCC TGC CTG GAC GCC GAC ACG CGC CCC GCT CGC AGC    513
Asn Ala Phe Arg Ser Cys Leu His Ala Asp Thr Arg Pro Ala Arg Ser
    100                 105                 110

GAG CGG CGC GCG AGC GCC GCG GTC GAA AAC CAC GTG CTC TTC TCC ATC    561
Glu Arg Arg Ala Ser Ala Ala Val Glu Asn His Val Leu Phe Ser Ile
115                 120                 125                 130

GCC CGT CCG CGC CCA ATA GAC TCG GGG CTC TAC TTT CTG CGC GTC GGC    609
Ala Arg Pro Arg Pro Ile Asp Ser Gly Leu Tyr Phe Leu Arg Val Gly
                135                 140                 145

ATC TAC GGC GGC ACC GCG GGC AGC GAG CGC CGC CGA GAC GTC TTT CCC    657
Ile Tyr Gly Gly Thr Ala Gly Ser Glu Arg Arg Arg Asp Val Phe Pro
            150                 155                 160
```

FIG. 2C

```
TTG GCC GCG TTT GTA CAC AGC TTC GGT GAG CCC GGA GAC CCA GAG GCC    705
Leu Ala Ala Phe Val His Ser Phe Gly Glu Pro Gly Asp Pro Glu Ala
        165                 170                 175

GCG GCG CGC ACC CCG GCA CCG TCG AGG CAG TCC AGG CGG GGT GCG AGC    753
Ala Ala Arg Thr Pro Ala Pro Ser Arg Gln Ser Arg Pro Ala Ala Ser
    180             185                     190

GGC CTG ACC AGC TCG GCG AGC CTC TAC GAC CGC GCG CTG GCG CGT TCC    801
Gly Leu Thr Ser Ser Ala Ser Leu Tyr Asp Arg Ala Leu Ala Arg Ser
195                 200                 205                 210

CCG CAG GCG CCG CCA CCA CGC CCG GCC CCA CCG CGA GCA GCG AGA GCG    849
Pro Gln Ala Pro Pro Pro Arg Pro Ala Pro Pro Arg Ala Ala Arg Ala
            215                 220                 225

GGG CCG CGA CGC CCA GAG AGG GTC GAC GAG ACG ACG GAA GTC GAG GCC    897
Gly Pro Arg Arg Pro Glu Arg Val Asp Glu Thr Thr Glu Val Glu Ala
            230                 235                 240

GCG ACG AGA GCG GGC TCG GCG TTT GCC CTC ACC ACG CCC CCG GCC GGC    945
Ala Thr Arg Ala Gly Ser Ala Phe Ala Leu Thr Thr Pro Pro Ala Gly
        245                 250                 255
```

FIG. 2D

```
CCG ACC GCC AGC CCC GCC GCC AGC CCC TCC CGT GCC TTT AGC GCG GCC   993
Pro Thr Ala Ser Pro Ala Ala Ser Pro Ser Arg Ala Phe Ser Ala Ala
    260                 265                 270

GCC CCG GCC GCC GCT GCG CAG CCG GCC GGA GAC ACG CCC GCT CGC TTC  1041
Ala Pro Ala Ala Ala Ala Gln Pro Ala Gly Asp Thr Pro Ala Arg Phe
275                 280                 285                 290

CGG CGC CAA CTG GCG TGG ATC CTA GTG CCT CTG TGC GTG CTG GTG CTG  1089
Arg Arg Gln Leu Ala Ser Ile Leu Val Pro Leu Cys Val Leu Val Leu
                295                 300                 305

CTG CTG CTT GCG CTC TGC GCC GCG ACG GTA AAC TGC GCG CTG CGC CGT  1137
Leu Leu Leu Ala Leu Cys Ala Ala Thr Val Asn Cys Ala Leu Arg Arg
            310                 315                 320

CGC CTG CTG CCG TGC TCT CGG CGC GTT TAC AAG CCG CGG ACG TGC GCG  1185
Arg Leu Leu Pro Cys Ser Arg Arg Val Tyr Lys Pro Arg Thr Cys Ala
        325                 330                 335

GCG TGC GGG AGC GGC ACT TGC GCG GGG CGG CCC CCC TGC CGC GGC GCG  1233
Ala Cys Gly Ser Gly Thr Cys Ala Gly Arg Pro Pro Cys Arg Gly Ala
    340                 345                 350
```

*FIG. 2E*

```
GCA CCG AGC GCC CCA GCC ACC GTC GTG GCA CTG GGC TCC CGG CCA AAG   1281
Ala Pro Ser Ala Pro Ala Thr Val Val Ala Leu Gly Ser Arg Pro Lys
355                 360                 365                 370

GCG CCC CCC CTC GCC ACC ATC AGC GAA GAA TAAACGCCGC GCGCGGCAAA    1331
Ala Pro Pro Leu Ala Thr Ile Ser Glu Glu ---
                375                 380

CGATCTCGCT CGCGTGTGTC TTGGTTTCTG GGCGGCGGGC GGGGTGGGGA GCGGCCAAAG 1391

CGGAGGAAGA CCGGGGGCAG GAGCTGCGTG CAGGGCCGAG CCGTTGAGCG GCCCGACCGC 1451

CGCCGGGTTG TTAAATGGGT CTCGCGCGGC TGGTGGTTCC ACACTGGGCC GGAGAACCAG 1511

CGCGACGTTC GCTGCGTGTG GAACCACGAG CTGGGTTCCG GGAACGGCG CACGCGAGAG 1571

GGTTCGAAAA GGGCATTTGG CA ATG CAA CCC ACC GCG CCG CCC CGG CGG CGG  1623
                         Met Gln Pro Thr Ala Pro Pro Arg Arg Arg
                          1               5                  10

TTG CTG CCG CTG CTG CTG CCG CAG CTA TTG CTT TTC GGG CTG ATG GCC   1671
Leu Leu Pro Leu Leu Leu Pro Gln Leu Leu Leu Phe Gly Leu Met Ala
                15                  20                  25
```

FIG. 2F

```
GAG GCC GAG CCC GCG ACC GAA ACC CCG GGC TCG GCT TCG GTC GAC ACG     1719
Glu Ala Glu Pro Ala Thr Glu Thr Pro Gly Ser Ala Ser Val Asp Thr
         30                  35                  40

GTC TTC ACG GCG CGC GCC GGC GCG CCC GTC TTT CTC CCA GGG CCC GCG     1767
Val Phe Thr Ala Arg Ala Gly Ala Pro Val Phe Leu Pro Gly Pro Ala
         45                  50                  55

GCG CGC CCG GAC GTG CGC GCC GTT CGC GGC TGG AGC GTC CTC GCG GGC     1815
Ala Arg Pro Asp Val Arg Ala Val Arg Gly Trp Ser Val Leu Ala Gly
     60                  65                  70

GCC TGC TCG CCG CCC GTG CCG GAG CCC GTC TGC CTC GAC GAC CGC GAG     1863
Ala Cys Ser Pro Pro Val Pro Glu Pro Val Cys Leu Asp Asp Arg Glu
 75                  80                  85                  90

TGC TTC ACC GAC GTG GCC CTG GAC GCC GCC TGC CTG CGA ACC GCC CGC     1911
Cys Phe Thr Asp Val Ala Leu Asp Ala Ala Cys Leu Arg Thr Ala Arg
             95                 100                 105

GTG GCC CGG CTG GCC ATC GCG GAG CTC GCC GAG CGG CCC GAC TCG ACG     1959
Val Ala Pro Leu Ala Ile Ala Glu Leu Ala Glu Arg Pro Asp Ser Thr
        110                 115                 120
```

FIG. 2G

```
GTG GAC AAA GAG TTT GTT CTC GCC GAC CCG CAC GTC TCG GCG CAG CTG   2007
Gly Asp Lys Glu Phe Val Leu Ala Asp Pro His Val Ser Ala Gln Leu
        125                 130                 135

GGT CGC AAC GCG ACC GGG GTG CTG ATC GCC GCC GCA GCC GAG GAG GAC   2055
Gly Arg Asn Ala Thr Gly Val Leu Ile Ala Ala Ala Ala Glu Glu Asp
    140                 145                 150

GGC GGC GTG TAC TTC CTG TAC GAC CGG CTC ATC GGC GAC GCC GGC GAC   2103
Gly Gly Val Tyr Phe Leu Tyr Asp Arg Leu Ile Gly Asp Ala Gly Asp
155                 160                 165                 170

GAG GAG ACG CAG TTG GCG CTG ACG CTG CAG GTC GCG ACG GCC GGC GCG   2151
Glu Glu Thr Gln Leu Ala Leu Thr Leu Gln Val Ala Thr Ala Gly Ala
            175                 180                 185

CAG GGC GCC GCG CGG GAC GAG GAG AGG GAA CCA GCG ACC GGG CCC ACC   2199
Gln Gly Ala Ala Arg Asp Glu Glu Arg Glu Pro Ala Thr Gly Pro Thr
            190                 195                 200

CCC GGC CCG CCG CCC CAC CGC ACG ACG ACA CGC GCG CCC CCG CGG CGG   2247
Pro Gly Pro Pro Pro His Arg Thr Thr Thr Arg Ala Pro Pro Arg Arg
        205                 210                 215
```

*FIG. 2H*

```
CAC GGC GCG CGC TTC CGC GTG CTG CCG TAC CAC TCC CAC GTA TAC ACC    2295
His Gly Ala Arg Phe Arg Val Leu Pro Tyr His Ser His Val Tyr Thr
    220                 225                 230

CCG GGC GAT TCC TTT CTG CTA TCG GTG CGT CTG CAG TCT GAG TTT TTC    2343
Pro Gly Asp Ser Phe Leu Leu Ser Val Arg Leu Gln Ser Gln Phe Phe
235                 240                 245                 250

GAC GAG GCT CCC TTC TCG GCC AGC ATC GAC TGG TAC TTC CTG CGG ACG    2391
Asp Glu Ala Pro Phe Ser Ala Ser Ile Asp Trp Tyr Phe Leu Arg Thr
                255                 260                 265

GCC GGC GAC TGC GCG CTC ATC CGC ATA TAC GAG ACG TGC ATC TTC CAC    2439
Ala Gly Asp Cys Als Leu Ile Arg Ile Tyr Glu Thr Cys Ile Phe His
            270                 275                 280

CCC GAG GCA CCG GCC TGC CTG CAC CCC GCC GAC GCG CAG TGC AGC TTC    2487
Pro Glu Ala Pro Ala Cys Leu His Pro Ala Asp Ala Gln Cys Ser Phe
        285                 290                 295

GCG TCG CCG TAC CGC TCC GAG ACC GTG TAC AGC CGG CTG TAC GAG CAG    2535
Ala Ser Pro Tyr Arg Ser Glu Thr Val Tyr Ser Arg Leu Tyr Glu Gln
    300                 305                 310
```

*FIG. 2I*

```
TGC CGC CCG GAC CCT GCC GGT CGC TGG CCG CAC GAG TGC GAG GGC GCC    2583
Cys Arg Pro Asp Pro Ala Gly Arg Trp Pro His Glu Cys Glu Gly Ala
315                 320                 325                 330

GCG TAC GCG GCG CCC GTT GCG CAC CTG CGT CCC GCC AAT AAC AGC GTA    2631
Ala Tyr Ala Ala Pro Val Ala His Leu Arg Pro Ala Asn Asn Ser Val
                335                 340                 345

GAC CTG GTC TTT GAC GAC GCG CCG GCT GCG GCC TCC GGG CTT TAC GTC    2679
Asp Leu Val Phe Asp Asp Ala Pro Ala Ala Ala Ser Gly Leu Tyr Val
            350                 355                 360

TTT GTG CTG CAG TAC AAC GGC CAC GTG GAA GCT TGG GAC TAC AGC CTA    2727
Phe Val Leu Gln Tyr Asn Gly His Val Glu Ala Trp Asp Tyr Ser Leu
        365                 370                 375

GTC GTT ACT TCG GAC CGT TTG GTG CGC GCG GTC ACC GAC CAC ACG CGC    2775
Val Val Thr Ser Asp Arg Leu Val Arg Ala Val Thr Asp His Thr Arg
    380                 385                 390

CCC GAG GCC GCA GCC GCC GAC GCT CCC GAG CCA GGC CCA CCG CTC ACC    2823
Pro Glu Ala Ala Ala Ala Asp Ala Pro Glu Pro Gly Pro Pro Leu Thr
395                 400                 405                 410
```

FIG. 2J

```
AGC GAG CCG GCG GGG GCG CCC ACC GGG CCC GCG CCC TGG CTT GTG GTG    2871
Ser Glu Pro Ala Gly Ala Pro Thr Gly Pro Ala Pro Trp Leu Val Val
                415                 420                 425

CTG GTG GGC GCG CTT GGA CTC GCG GGA CTG GTG GGC ATC GCG GCC CTC    2919
Leu Val Gly Ala Leu Gly Leu Ala Gly Leu Val Gly Ile Ala Ala Leu
            430                 435                 440

GCC GTT CGG GTG TGC GCG CGC CGC GCA AGC CAG AAG CGC ACC TAC GAC    2967
Ala Val Arg Val Cys Ala Arg Arg Ala Ser Gln Lys Arg Thr Tyr Asp
        445                 450                 455

ATC CTC AAC CCC TTC GGG CCC GTA TAC ACC AGC TTG CCG ACC AAC GAG    3015
Ile Leu Asn Pro Phe Gly Pro Val Tyr Thr Ser Leu Pro Thr Asn Glu
    460                 465                 470

CCG CTC GAC GTG GTG GTG CCA GTT AGC GAC GAC GAA TTT TCC CTC GAC    3063
Pro Leu Asp Val Val Val Pro Val Ser Asp Asp Glu Phe Ser Leu Asp
475                 480                 485                 490

GAA GAC TCT TTT GCG GAT GAC GAC AGC GAC GAT GAC GGG CCC GCT AGC    3111
Glu Asp Ser Phe Ala Asp Asp Asp Ser Asp Asp Asp Gly Pro Ala Ser
                495                 500                 505
```

*FIG. 2K*

```
AAC CCC CCT GCG GAT GCC TAC GAC CTC GCC GGC GCC CCA GAG CCA ACT    3159
Asn Pro Pro Ala Asp Ala Tyr Asp Leu Ala Gly Ala Pro Glu Pro Thr
            510                 515                 520

AGC GGG TTT GCG CGA GCC CCC GCC AAC GGC ACG CGC TCG AGT CGC TCT    3207
Ser Gly Phe Ala Arg Ala Pro Ala Asn Gly Thr Arg Ser Ser Arg Ser
        525                 530                 535

GGG TTC AAA GTT TGG TTT AGG GAC CCG CCT GAA GAC GAT GCC GCG CCA    3255
Gly Phe Lys Val Trp Phe Arg Asp Pro Pro Glu Asp Asp Ala Ala Pro
    540                 545                 550

GCG CGG GCC CCG GCC GCA CCA GAT TAC ACC GTG GTA GCA GCG CGA CTC    3303
Ala Arg Ala Pro Ala Ala Pro Asp Tyr Thr Val Val Ala Ala Arg Leu
555                 560                 565                 570

AAG TCC ATC CTC CGC TAGGCCCCCC CCCCCGCGCG CGCGCTGTGC CGTCTGACGG    3358
Lys Ser Ile Leu Arg
            575

AAAGCACCCG CGTGTAGGGC TGCATATAA ATG GAG CGC TCA CAC AAA GCC TCG    3411
                                Met Glu Arg Ser His Lys Ala Ser
                                 1               5
```

FIG. 2L

```
TGC GGC TGC TTC GAA GGC ATG GAG AGT CCA CGC AGC GTC GTC AAC GAA    3459
Cys Gly Cys Phe Glu Gly Met Glu Ser Pro Arg Ser Val Val Asn Glu
     10                  15                  20

AAC TAT CGA GGC GCT GAT GAG CCC GAT GCA GCG CCC CCC TCA CCG CCG    3507
Asn Tyr Arg Gly Ala Asp Glu Ala Asp Ala Ala Pro Pro Ser Pro Pro
 25                  30                  35                  40

CCG GAG GGC TCC ATC GTG TCC ATC CCC ATC CTC GAG CTC ACC ATC GAG    3555
Pro Glu Gly Ser Ile Val Ser Ile Pro Ile Leu Glu Leu Thr Ile Glu
                 45                  50                  55

GAC GCG CCG GCC AGC GCA GAA GCA ACC GGC ACC GGG GCA GCC GCA CCC    3603
Asp Ala Pro Ala Ser Ala Glu Ala Thr Gly Thr Ala Ala Ala Ala Pro
             60                  65                  70

GCT GGG CGC ACG CCA GAC GCG AAC GCA GCA CCC GGC GGC TAC GTG CCA    3651
Ala Gly Arg Thr Pro Asp Ala Asn Ala Ala Pro Gly Gly Tyr Val Pro
         75                  80                  85

GTT CCC GCG GCG GAC GCG GAC TGC TAT TAT AGC GAA AGC GAC AGC GAG    3699
Val Pro Ala Ala Asp Ala Asp Cys Tyr Tyr Ser Glu Ser Asp Ser Glu
     90                  95                 100
```

FIG. 2M

```
ACG GCA GGC GAG TTT TTG ATA CGC ATG GGG CGG CAG CAG CGG CGG CGG   3747
Thr Ala Gly Glu Phe Leu Ile Arg Met Gly Arg Gln Gln Arg Arg Arg
105                 110                 115                 120

CAT CGG CGG CGG CGC TGC ATG ATA GCA GCG GCC CTG ACT TGC ATT GGC   3795
His Arg Arg Arg Arg Cys Met Ile Ala Ala Ala Leu Thr Cys Ile Gly
                125                 130                 135

CTC GGG GCC TGC GCG GCG GCG GCA GCG GCA GGC GCC GTC CTG GCG TTG   3843
Leu Gly Ala Cys Ala Ala Ala Ala Ala Ala Gly Ala Val Leu Ala Leu
            140                 145                 150

GAG GTA GTG CCC CGG CCC TGAGGCGGGG CCCGACTGTC CCCCTCCCCC          3891
Glu Val Val Pro Arg Pro
        155

CTCCCCCCGT CCGCCCCCCG TCCGCCCGCG AGTAAAGGCT GTCTAATTTT TTCCGCACGC 3951

CCGCGCCTGT CTTTTTTGTG AGGGGAAGAG GGGAGGGCGG GGAAGAGGGG AAGGAGGGGA 4011

AGAGGCGCCA AGCGGCGAGC CGCCGGTCCC GCCGAATGGG TCCGGGCTCG ATAGGCATAC 4071

CGGATGCTTG CGGCTGGCCG GTGCGCTGGA CGACCCAGGC GAAGGAGGGG AAGGAGGGGA 4131

AGAGGGGATT CGGGCCGGCC GCAGCGAGCG GTCAAAGCTC CGGCTCCCCC CTCCCCTCC  4190
```

FIG. 2N

MUTANTS AND VACCINES OF THE INFECTIOUS BOVINE RHINOTRACHEITIS VIRUS

This application is a continuation of Application Ser. No. 08/199,172 filed Aug. 9, 1994 now abandoned, which is a 371 of PCT/FR93/00642 filed Jun. 25, 1992.

FIELD OF THE INVENTION

The subject of the present invention is segments of the genome of the infectious bovine rhinotracheitis herpes-virus (IBR), contained in its short unique region, and encoding especially the gİ glycoproteins. The present invention relates to the DNA segments containing the gene encoding these antigenic glycoproteins and containing potential promoter sequences up to 400 nucleotides in 5' of each gene, which segments are useful as possible source of BHV-1 promoters, for the expression of the genes for producing this and other glycoproteins, such as gE which in turn can be used to induce antibodies recognizing them, as potential sites for the insertion of foreign genes, and as potential sites for deletion or insertion in order to prevent the synthesis of these antigenic glycoproteins by the virus.

The subject of the invention is especially an insertion region in the genomic DNA of the bovine herpesvirus (BHV) comprising three open reading frames located in the short unique region (Us) of the genome corresponding to the nucleotide sequence SEQ ID No:1 of FIG. 2.

Such an insertion region may comprise, for example the DNA sequence delimited by nucleotides 172 and 1311 of the sequence presented in FIG. 2.

Another insertion region may comprise the DNA sequence delimited by nucleotides 1594 and 3318 of the sequence presented in FIG. 2.

The subject of the invention is also plasmids comprising the insertion region according to the invention.

The plasmids according to the invention may also contain a foreign gene, isolated from an agent pathogenic for bovines, inserted in the said insertion region.

The said foreign gene is preferably chosen from a group essentially comprising the bovine coronavirus, the bovine rotavirus, the bovine leukosis virus, the foot-and-mouth virus, the mucosal disease virus, Salmonella, *E. coli*, where the said foreign gene is placed under the control of a promoter capable of directing its expression.

The subject of the present invention is particularly mutants of the IBR (BHV-1) virus containing mutations caused by total or partial deletion and/or by insertion in the said region and especially in the gİ-encoding gene, or the surrounding non-coding sequences, such that there is no longer any expression of the glycoprotein encoded by the gene which has been mutated or rendered inactive. Consequently, animals vaccinated with these mutants do not develop antibodies against the viral glycoprotein and can be serologically distinguished from animals infected by field BHV-1 strains and other vaccinal strains currently used.

The subject of the present invention is also the use of the mutant BHV-1 viruses described above as vectors for expression of foreign genes to prepare vaccines against bovine (ruminant) diseases. As above, animals vaccinated with these expression vectors do not develop antibodies against the viral glycoprotein and can be serologically distinguished from animals infected by field BHV-1 strains.

The recombinant BHV viruses may comprise a promoter for the insertion region, which promoter is functional in a host cell for the expression of the said foreign gene. The recombinant BHV viruses are designed so that at least one polypeptide encoded by the said foreign gene and at least one polypeptide encoded by the said BHV genomic DNA are expressed.

The subject of the present invention is furthermore the methods for producing the deleted mutants, the methods for producing the expression vectors and the methods for using the vaccines prepared from the deleted viruses or from the expression vectors expressing foreign genes.

The subject of the invention is also the vaccines comprising a recombinant BHV virus according to the invention. The vaccines may consist of the live virus, or of inactivated viral particles, or of subunits of the particles, with, preferably, a conventional adjuvant.

The subject of the present invention is also the expression of the BHV-1 gİ gene in various expression systems in order to use the expression products obtained as antigens. The present invention also relates to the preparation of serological reagents from the BHV-1 gİ antigens alone or with BHV-I gE antigens.

The subject of the present invention is furthermore the use of the BHV-1 gİ and optionally BHV-1 gE antigens to detect the presence of specific antibodies in the serum of bovines infected by BHV-1.

The present invention finally describes, for the first time, a 4190 bp DNA sequence contained in the Us region of the BHV-1 genome and encoding the genes homologous to HSV-1 gİ, HSV-1 gE and HSV-1 US9.

BACKGROUND OF THE INVENTION

Infectious bovine rhinotracheitis (IBR) is an acute and contagious infectious bovine disease, often aggravated by bacterial complications (Pastoret P. P., Ann. Med. Vet., 122, 371–391, 1978). This disease occurs, either in a respiratory form (IBR proper), which is predominant and which mainly affects young bovines, or in a genital form, infectious pustular vulvovaginitis (IPV) which has been historically important but which is currently more rare (Yates W. P., Can. J. Comp. Med., 46, 225–263, 1982). IBR is one of the principal causes of respiratory ailments in bovines and causes considerable economic losses both in the dairy industry and in meat production. Given the economic importance of this disease, sanitary barriers aimed at banning the import of infected animals have been introduced by a number of countries.

This disease is of viral nature and its etiological agent has been identified as type 1 bovine herpesvirus (BHV-1) (Madin S. H. et al., Science, 124, 721–722, 1956). This virus is classified in the family Herpesviridae and belongs more specifically to the subfamily Alphaherpesviridae of which the prototype is type 1 human herpes simplex virus (HSV-1) (Armstrong J. A. et al., Virology, 14, 276–285, 1961; Roizman B. et al., Arch. Virol., 123, 425–449, 1992). As most herpesviruses, the BHV-1 virus can be present in the latent state in its host and be reactivated under certain circumstances (stress, transport and the like). The control of this disease is based both on sanitary prophylaxis and on medical prophylaxis.

The clinical diagnosis is rendered difficult in the serious superinfected forms, which show, in this case, similarities with other bovine respiratory infections, and is not always easy to implement. Definite proof of an IBR disease can be provided only with laboratory tests (Gilbert Y. et al., Rev. Med. Vet., 3, 383–389, 1976; Fedida H. and Dannacher G., Bull. Lab. Vet., 5, 35–46, 1982). The isolation of the virus during cell culture from ecouvillonnages produced on the suspected animals remains the best means of diagnosing the disease. But this technique is slow and in particular cumbersome to implement. Consequently, simpler and more rapid techniques based on the detection of the BHV-1 antigens or, increasingly, on the detection of specific antibodies in the serum of the suspected animals, are now preferred in its place. Numerous tests using the ELISA technique are currently on the market (Cheng-Feng Z. and Forbes S. D., New Zealand, Vet. J., 36, 204–205, 1988). Seroneutralization remains, however, the official technique during European or international commercial transactions.

The control of IBR is based mainly on vaccination (Straub O. C. and Mawhinney I. C., Vet. Rec., 122, 407–411, 1988).

Three types of vaccines have been used to protect bovines against IBR (Kit M. et al., European Patent Application No. 0 316 658 A1, 1988).

The vaccines based on attenuated viruses obtained by a large number of successive passages of the pathogenic viruses on cells of bovine origin, by adaptation of these same viruses on cells of an origin other than bovine, or by selection of heat-stable spontaneous viral mutants. These vaccines are easy to produce, of relatively low cost and injectable.

They induce a rapid protection of long duration (Casselberry N. H., J.A.V.M.A., 152, 853–856, 1968). They have, nevertheless, a number of disadvantages since they possess a residual virulence for gestating cows (abortions) and can recover their original virulence by reversion. Furthermore, the possibility of establishment of a latency following their injection cannot be excluded. Heat-sensitive strains have been developed in order to overcome these disadvantages but they require an administration by the intranasal route, which is not very practical (Kahrs R. F. et al., J.A.V.M.A., 163, 437–441, 1973).

The vaccines prepared based on inactivated viruses, obtained by treatment of the pathogenic virus with physical or chemical agents (Durand H. et al, Bull. Soc. Vet. Pr. 65, 193–204, 1981). The manufacture of these vaccines is a lot more expensive since it necessitates numerous controls. These vaccines are also less effective than the attenuated live vaccines and necessitate several successive administrations in the presence of adjuvant in order to induce a good protection.

The viral subunit vaccines are obtained by partial purification of the envelope glycoproteins responsible for the protective immunity (Babiuk L. A. et al., Virology, 159, 57–66, 1987), after culturing the BHV-1 virus. Perfectly innocuous, these vaccines too are of relatively high cost because of the purification step, the need to use an adjuvant and the multiple injections required to induce a protective immune response (Israel B. A. et al., Vaccine 6, 349–356, 1988).

The vaccines commonly used for controlling IBR are therefore far from being satisfactory, either because they possess a residual virulence, or because they are not very practical to use, or finally because they are relatively expensive. On the other hand, the main disadvantage of the three types of vaccines described above is that they do not permit differentiation between infected animals and vaccinated animals, a condition which is absolutely necessary in order to conduct a reasoned prophylaxis, by vaccination and simultaneous elimination of the infected animals, with a view to the eradication of IBR.

Experimental attenuated live vaccinal strains have been proposed as solutions to this problem. They were obtained by genetic recombination by deletion of the gene encoding thymidine kinase (Kit M. et al., European Patent Application No. 0 316 658 A1, 1988). These strains do not, however, make it possible to solve the problem caused by apparently healthy animals, but carriers of the virus in the latent state, which represent a potential reservoir for transmission of the disease. Neither do they permit differentiation between vaccinated animals and infected animals.

Other vaccines based on BHV-1 viruses deleted in the genes encoding thymidine kinase and the glycoprotein gIII (homologous to the glycoprotein gC of HSV-1) have been proposed (Kit M. et al., European Patent Application No. 0 326 127 A2, 1989) in order to differentiate the vaccinated animals from the infected animals. The equivalents of this glycoprotein in the herpesviruses HSV-1 (gC) and PRV (gIII) have proved to be non-essential for viral replication in vitro (Holland T. C. et al., J. Virol., 52, 566–574, 1984; Kit S. et al., Am. J. Vet. Res., 48, 780–793, 1987), but the glycoprotein gIII participates in an important fashion in the induction of neutralizing antibodies in animals immunized with BHV-1 (Collins J. K. et al., J. Virol., 52, 403–409, 1984) which might be responsible for a lower activity of these vaccines in the field.

The impossibility of distinguishing the infected animals from the immunized animals with the current commercial vaccines is the major obstacle to a policy for eradication of the disease in the countries affected. Incidentally, this situation also acts as a brake on international exchanges of animals since many countries demand that the bovines be seronegative with respect to BHV-1 during importations Any reasoned eradication policy involves the combined measures of sanitary prophylaxis (slaughtering) and medical prophylaxis (vaccination) In this perspective, an "ideal" vaccine is that which will make it possible to confer, at the best price, an early, satisfactory and lasting immunity, and which, if it is combined with a screening test which is simple to use, will permit an easy differentiation between vaccinated animals and infected animals.

SUMMARY OF THE INVENTION

A mutant BHV-1 virus, deleted in a gene encoding one or more minor viral glycoproteins not participating in an important fashion in the induction of protection, and used to prepare an inactivated, attenuated, or subunits vaccine, meets these multiple objectives.

BRIEF DESCRIPTION OF THE DRAWINGS

FIG. 2 shows the nucleotide sequence of the region covering gİ, gE and US9 genes of BHV-1.

DETAILED DESCRIPTION OF THE PREFERRED EMBODIMENTS

The BHV-1 genome

Figure 1:
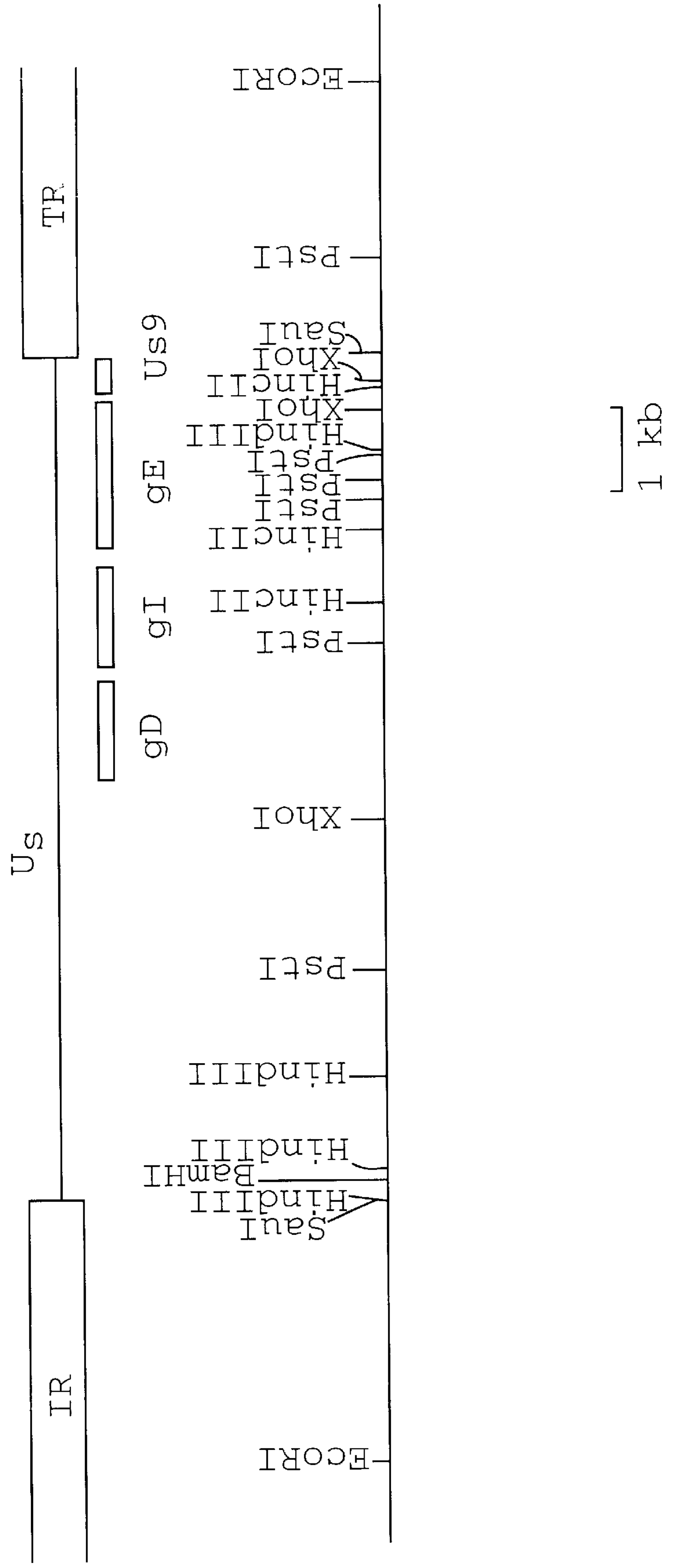
FIG. 1 shows a map of the Us region of the BHV genome with localization of the gD, gİ, gE and US9 genes with a restriction map facing thereto.

The structure of its genome makes it possible to classify the infectious bovine rhinotracheitis virus in group D of the herpesviruses to which the Aujeszky's disease virus (PRV), the type 1 and 4 equine herpesviruses, and that for varicella (VZV) (Roizman B. et al., Arch. Virol., 123, 425–449, 1992), also belong. The BHV-1 genome is a double-stranded linear DNA of about 140 kb, composed of a unique long sequence of 105 kb ($U_L$) and a unique short sequence of 11 kb ($U_S$), the latter being flanked by two inverted repeat regions of about 12 kb (internal repeat region (IR) and terminal repeat region (TR)). The $U_S$ part can be orientated in either direction relative to the $U_L$ part, conferring on the BHV-1 genome the property of existing in two isomeric forms (Wirth U. V. et al., J. Virol., 63, 4882–4889, 1989).

The analysis of restriction fragments after digestion of the viral DNA by restriction endonucleases has proved to be quite an appropriate tool for differentiation of the BHV-1 strains. It makes it possible, indeed, to classify them into three types associated with specific clinical manifestations (Bulach D. M. et Studdert M. J., Arch. Virol., 113, 17–34, 1990; Bratanich A. C. et al., J. Vet. Med., B38, 41–48, 1991; Engels M. et al., Arch. Virol., 67, 169–174, 1981).

Type BHV-1.1. Associated with IBR. The reference strain isolated from one IBR case is the Cooper strain (Zucheck F. and Chow T. L., J.A.V.M.A., 139, 236–237, 1961).

Type BHV-1.2. Associated with IPV. The reference strain isolated from one vulvovaginitis case is the K22 strain (Kendrick J. W. et al., Cornell Vet., 48, 458–495, 1958).

Type BHV-1.3. Associated with neurological symptoms. The reference strain is the BEHV N569 strain (French G. L., Austr. Vet., J., 38, 555–556, 1962).

Although BHV-1 encodes about 50 to 100 different genes, very few of them have been located on the physical map of the genome. The genes encoding thymidine kinase (Kit M. and Kit S., U.S. patent application Ser. No. 796,840, 1986; Mittal S. K. and Field H. J., J. Gen. Virol. 70, 901–918), DNA polymerase (Owen L. J. and Field H. J., Arch. Virol., 98, 27–38, 1988), the glycoprotein gI (Misra V. et al., Virology, 166, 542–549, 1988; Whitbeck J. C. et al., J. Virol., 62, 3319–3327, 1988), the glycoprotein gIII (Fitzpatrick D. R. et al., Virology, 173, 46–57, 1989) and the glycoprotein gIV (Tikoo S. K. et al., J. Virol., 64, 5132–5142, 1990) have been located on the BHV-1 genome, sequenced, and analyzed.

One aspect of the present invention comprises the identification of the location and the sequence of the BHV-1 genes encoding the glycoprotein homologous to the HSV-1 gI glycoprotein, and the sequence of the gene encoding the protein homologous to the HSV-1 US9 protein.

BHV-1 glycoproteins

The genome of the BHV-1 virus encodes at least 40 to 48 proteins (Misra V. et al., J. Virol., 40, 367–378; Wirth U. V. et al, J. Virol., 65, 195–205, 1991). An electrophoretic analysis, using SDS-PAGE, of the purified and radiolabeled BHV-1 virus reveals the presence of 25 to 33 structural polypeptides having a size of between 12 and 330 kDa. Among these structural polypeptides, 11 have been identified as being glycosylated (Misra V. et al., J. Virol., 40, 367–378, 1981) ; van Drunen Littel—van den Hurk S. and Babiuk L. A., J. Virol., 59, 401–410, 1986; van Drunen Littel—van den Hurk S. et al., Virology, 135, 466–479, 1984). The glycoproteins specific for the virus have a determinant role in the host-virus relationship since they are incorporated into the membrane of the infected cell and finally become constituents of the virion envelope. Consequently, they have important roles in the recognition, attachment and penetration of the virus into permissive cells, in the formation of syncytia and in the various responses of the bovine immune system to IBR infection, such as the neutralization of the virus and the immunological destruction of the infected cells. To date, four glycoproteins have been identified and characterized in the membrane of cells infected by BHV-1 and in the envelope of the virions. They are called gI, gII, gIII and gIV according to the nomenclature proposed for the first time in 1986 (van Drunen Littel—van den Hurk S. and Babiuk L. A., J. Virol., 59, 401–410, 1986).

Three of these glycoproteins (gI, gIII and gIV) have been more particularly studied because of their presence in large quantities in the virion envelope and because the majority of the anti-BHV-1 antibodies present in the serum of animals affected by IBR are directed against them; they are called, for this reason, major glycoproteins (van Drunen Littel—van den Hurk S. et al., Virology, 135, 466–479, 1984); van Drunen Littel—van den Hurk S. et al., Virology, 144, 216–227, 1985; Marshall R. L. et al., J. Virol., 57, 745–753, 1986; Babiuk L. A. et al., Virology, 159, 57–66, 1987). The genes encoding these 3 glycoproteins have all been isolated and sequenced. These three glycoproteins are recognized by monospecific antisera and by neutralizing monoclonal antibodies. They have apparent sizes on SDS-PAGE gel of 97 kDa (gIII), 77 kDa (gIV) and 130, 74 and 55 kDa (gI).

In addition to these three major glycoproteins, minor glycoproteins with molecular masses of about 115 kDa, 64 kDa and 45 kDa can also be observed. The 115 kDa glycoprotein, designated gII, is specific for the virus since it is precipitated by monoclonal antibodies recognizing BHV-1 (van Drunen Littel—van den Hurk S. et al., Virology, 135, 466–479, 1984), but up until now, it has not been possible to characterize the gene encoding this glycoprotein.

It has been demonstrated that, in herpesviruses, more than one glycoprotein is involved in the induction of neutralizing antibodies and cytotoxic lymphocytes which help in preventing infection and in curing an infection. For example, the monospecific antisera directed against each of the glycoproteins gB, gC, gD and gE of HSV-1 are capable of neutralizing the virus and initiating the complement-dependent lysis of the cells infected by the virus (Norrild B. et al., J. Virol., 32, 741–748, 1979). In the same manner, the monoclonal antibodies directed against the glycoproteins gB, gC, gD and gF of the type 2 herpes simplex virus (HSV-2) initiate the immunological lysis of the infected cells (Balachandran N. et al., Infect. Imm., 37, 1132–1137). Moreover, neutralizing antibodies have been produced from the glycoproteins gII, gIII and gp50 of PRV; the passive immunization of animals with monoclonal antibodies directed either against PRV gp50, or against PRV gIII, protects them from infection with the wild-type virus (Hampl H. et al., J. Virol., 52, 583–590, 1984; Ben Porat T. et al., Virology, 154, 325–334, 1986). Likewise, monoclonal antibodies directed against the glycoproproteins gp13, gp14 and gp17/18 of type 1 equine herpesvirus (EHV-1), used to inoculate hamsters, protects them passively against a virulent challenge with EHV-1 (Stokes A. et al., J. Gen. Virol., 70, 1173–1183, 1989; Shimizu M. et al., Arch. Virol., 104, 169–174, 1989). As regards the BHV-1 virus, the major glycoproteins gI, gIII and gIV induce high levels of neutralizing antibodies in bovines and participate in antibody-dependent cell cytotoxicity.

In order to develop a BHV-1 vaccine having a serological marker which permits differentiation between vaccinated animals and naturally-infected animals, it was necessary, in the present invention, to identify a gene encoding a BHV-1 glycoprotein which is not essential for the replication of the virus in vitro and which is not involved in an important fashion in the induction of the protective immune response.

The glycoprotein gI is homologous to the glycoprotein gB of HSV-1 and the PRV gII glycoprotein (Whitbeck J. C. et al., J. Virol., 62, 3319–3327, 1988; Misra V. et al., Virology, 166, 542–549, 1988). Numerous experimental data indicate that the HSV-1 gB and PRV gII genes are essential for the replication of the virus (Marlin S. D. et al., J. Virol., 53, 128–138, 1985; Lawrence W. C. et al., J. Virol., 60, 405–414, 1986; Bzik D. J. et al., Virology, 137, 185–190, 1984). Recently, it has been shown that the product of the BHV-1 gI gene was itself essential for the viral replication and that it could functionally complement the PRV gII glycoprotein in PRV gII-mutants (Kopp A. and Mettenleiter T. C., J. Virol., 66, 2754–2762, 1992). Substantial convergence therefore exists between experimental results to indicate that the "gB-equivalent" glycoproteins are essential for the replication of alphaherpesviruses. Consequently, the gene encoding BHV-1 gI cannot be a candidate to serve as serological marker for BHV-1 vaccines.

The BHV-1 gIII glycoprotein is homologous to the HSV-1 gC glycoprotein (Fitzpatrick D. R. et al., Virology, 173, 44–57, 1989). HSV-1 and HSV-2 mutants incapable of synthesizing the glycoprotein gC have been isolated (Holland T. C. et al., J. Virol., 52, 566–574; 1984; Johnson D. C. et al., J. Virol., 58, 36–42, 1986). Likewise, a deleted PRV mutant for the tk and gIII genes has been isolated (Kit S. et al., Am. J. Vet. Res., 48, 780–793, 1987). Based on the same principle, the same authors obtained a deleted BHV-1 virus mutant for the tk and gIII genes which theoretically makes it possible to distinguish the vaccinated bovines from the bovines naturally infected by BHV-1 (Kit H. et al., European Patent Application Number 0 316 658, 1988). This patent does not interfere with the present invention.

Although not essential for replication, the BHV-1 gIII glycoprotein is however predominantly recognized by neutralizing monoclonal antibodies (Ludwig G. V. and Letchworth G. J. III, J. Virol., 61, 3292–3294, 1987; van Drunen Littel—van den Hurk S. et al., Virology, 135, 466–479, 1984; van Drunen Littel—van den Hurk S. et al., Vaccine, 8, 358–368, 1990) and permits an effective protection of the immunized animals (Babiuk L. A. et al., Virology, 159, 57–66, 1987). This glycoprotein, like all the other "gC-equivalent" glycoproteins in alphaherpesviruses, therefore has an important role in the induction of a protective immunity against BHV-1. The gene encoding BHV-1 gIII is therefore also not a good candidate for producing a deleted BHV-1 virus which will serve for the preparation of vaccines.

The BHV-1 gIV glycoprotein is homologous to the HSV-1 gD glycoprotein (Tikoo S. K. et al., J. Virol., 64, 5132–5142, 1990). Like the gI and gIII glycoproteins, it has a major role in the induction of the protective anti-BHV-1 immune response in infected bovines. The gene encoding BHV-1 gIV is present in the $U_S$ part of the genome, as is the case for the other "gD-equivalent" glycoproteins already characterized in HSV-1, PRV and EHV-1 (Tikoo S. K. et al., J. Virol., 64, 5132–5142, 1990; Petrovskis E. A. et al., J. Virol., 59, 216–223, 1986; McGeoch D. J. et al., J. Mol. Biol. 181, 1–13, 1985; Audonnet J. C. et al., J. Gen. Virol., 71, 2969–2978, 1990). The HSV-1 gD and PRV gp50 proteins are thought to be essential for an early stage of the process of penetration of the virus into cells (Sodora et al., J. Virol., 65, 4432–4441, 1991; Rauh I. and Mettenleiter T., J. Virol., 65, 5348–5356, 1991). Its essentialness for the replication of BHV-1 has not yet been demonstrated, contrary to HSV-1 gD (Longnecker R. and Roizman B., Science, 236, 573–576, 1987). The glycoprotein gIV plays, moreover, a major role in viral immunogenicity. The majority of the monoclonal antibodies derived from a cellular fusion using splenocytes from mice immunized with whole BHV-1 virus are indeed directed against the glycoprotein gIV (Marshall R. L. et al., Virology, 165, 338–347, 1988; Chang L. W. S. et al., Arch. Virol., 88, 203–215, 1986). Furthermore, these antibodies possess a neutralizing activity, even in the absence of complement (van Drunen Littel—van den Hurk S. et al., J. Clin. Microbiol., 23, 274–282, 1986) and are involved in antibody-dependent cell lysis (Ludwig G. V. and Letchworth G. J. III, J. Virol., 61, 3292–3294, 1987).

Finally, it is possible to protect calves against a BHV-1 challenge by immunizing them with the purified gIV glycoprotein (Babiuk L. A. et al., Virology, 159, 57–66, 1987). It therefore appears that the glycoprotein gIV too does not constitute a good target for producing deleted BHV-1 mutants.

Genes for glycoproteins which are not essential for the replication of BHV-1 in vitro, and which can be used as serological markers, can in fact be searched out among the genes located on the $U_S$ part of the BHV-1 genome.

In the present invention, it has been possible, for the first time, to identify, clone and sequence the BHV-1 genes encoding the proteins homologous to HSV-1 gİ and HSV-1 US9. Furthermore, in the present invention, it has been possible to show for the first time that the gene encoding the BHV-1 gİ glycoprotein is not essential for viral replication in vitro. Consequently, it has been possible for the first time to create mutations by genetic recombination in the BHV-1 gİ gene. Like for the deletion and/or insertion mutations in the gE gene, these mutant viruses can no longer synthesize the antigenic polypeptides encoded by the gİ genes. Consequently, the animals immunized with vaccines prepared from the mutant viruses described by the present invention will not make antibodies against the BHV-1 gİ, or gİ and gE glycoproteins if they are deleted in both genes It will therefore be possible to distinguish the vaccinated animals from the animals infected by the field BHV-1 strains, thereby making it possible to envisage the eradication of the IBR disease by the application of a medical prophylaxis which does not interfere with the sanitary prophylactic measures The expression of the glycoproteins encoded by the BHV-1 gİ and BHV-1 gE genes in an appropriate expression system makes it possible to produce the antigens necessary for the detection of the infected animals.

The vaccines according to the invention may be live or inactivated vaccines based on BHV-1 virus deleted at least in the gene encoding gİ. Preferably, the virus used may contain an additional deletion in the gene encoding the glycoprotein gE. The vaccines based on envelope glycoproteins and/or purified proteins or polypeptides obtained by purification from the deleted BHV-1 virus, are particularly preferred. The process permitting the production of these purified subunits is well known (Babiuk L. A. et al., Virology, 159, 57–66, 1987).

EXAMPLE 1

Cloning and partial sequencing of the BHV-1 $U_S$ region

A. Virus and culture of the virus

The virus used as parental virus is the ST strain of BHV-1, producing strain for the RHONE MERIEUX vaccines. This strain was isolated in 1970 from a bovine suffering from infectious bovine rhinotracheitis.

For the transfection experiments, the virus was cultured on IPB3 cells (semiestablished line from bovine fetal lung). For the isolation of the recombinant viruses, the viruses were cultured on RV cells (semiestablished line from calf kidney). All the cells were cultured in Dulbecco's modified Eagle medium (DHEM) containing 5% fetal calf serum.

B. Purification of BHV-1 and extraction of the viral DNA

The purified viral DNA necessary for the cloning experiments and for the Southern blot analyses was prepared from purified virus. The purification of the virus is performed starting with an infected culture exhibiting 100% cytopathogenic effect. The culture supernatant is clarified by centrifugation at 3800 g for 15 min in order to remove the cell debris. The virions present in the supernatant are then concentrated by sedimentation at 236,000 g for 1 hour, taken up in TBSA buffer (10 mM Tris, pH 7.5; 136 mM NaCl, 2.6 mM KCl; 20 mM Mg $Cl_2$; 1.8 mM $CaCl_2$; 1% bovine serum albumin) and loaded onto a 30% to 60% (weight/weight) sucrose step gradient in TBSA. After isopycnic ultracentrifugation (88,000 g, 18 hours), the viral band is recovered and diluted in 4 volumes of TBSA. The purified virions are then concentrated by a new ultracentrifugation (272,000 g, 1 hour) and taken up in a small volume of TBSA. The extraction of viral DNA from the purified viruses is then performed according to a standard technique (Maniatis T. et al., Molecular cloning: a laboratory manual, Cold Spring Harbor Laboratory, Cold Spring Harbor, N.Y., 1982).

The infectious viral DNA necessary for the transfection experiments is prepared according to a technique described by Hirt (Hirt B., J. Mol. Biol., 26, 365–369, 1967). When the infected cells show an onset of cytopathogenic effect, the culture medium is removed and the cells are placed in contact, for a few minutes, with a solution of TE (10 mM Tris, pH 8.0, 1 mM EDTA) containing 1% SDS in an amount of 1 ml per $5 \cdot 10^6$ to $10^7$ cells. Proteinase K is then added to this solution so as to obtain a final concentration of 200 $\mu$g/ml. After incubation for one hour at 37° C., a 5M NaCl solution is added so as to obtain a 1M NaCl final concentration and the mixture is placed overnight at 0° C. A centrifugation (12,000 g, 30 min) makes it possible to recover the supernatant which is then incubated in the presence of proteinase K 200 $\mu$g/ml final, at 37° C. for one hour. After two phenolchloroform extractions, the aqueous phase is collected and precipitated with 2.5 volumes of absolute ethanol overnight at −20° C. After centrifugation, the pellet is taken up in TE.

C. Cloning of the 16 kb EcoRI fragment

The 16.4 kb EcoRI fragment containing the entire $U_S$ region and part of the repeat regions of the BHV-1 ST strain was cloned into the pBluescript SK+ vector (Stratagene) digested with EcoRI. Competent bacteria, *Escherichia coli* NM 522, were transformed with the ligation product and the clones obtained were characterized by restriction analysis according to standard techniques (Maniatis et al., 1982). The clone containing the 16.4 kb EcoRI BHV-1 fragment was designated pBHV001.

D. Sequence of the BHV-1 $U_S$ fragment encoding the glycoproteins homologous to HSV-1 gİ, HSV-1 gE and the protein homologous to HSV-1 US9

The restriction map of the 16.4 kb EcoRI fragment was established with the enzymes BamHI, HincII, HindIII, PstI, SauI and XhoI (FIG. 1) and the sequence of a 4190 bp fragment (FIG. 2) was established from subclones in the pBluescript SK+ vector generated from digestions of the 16.4 kb EcoRI fragment using various restriction enzymes. Persons skilled in the art will recognize that there are multiple ways of generating these subclones. The complete sequence of both strands of the 4190 bp fragment was obtained using the modified enzyme T7 Sequenase (U.S. Biochemical Corporation) (Tabor S. and Richardson C. C., Proc. Nat. Acad. Sci., U.S.A., 84, 4767–4771, 1987). Standard chain termination reactions (Sanger F. et al., Proc. Nat. Acad. Sci. U.S.A., 74, 5463–5467, 1977) were performed on double-stranded templates previously denatured in a 0.4M NaOH solution (Hattori M. and Sakaki Y., Anal. Biochem., 152, 1015–1026, 1986). The forward and reverse M13 oligonucleotides were used to obtain the initial sequences at each end of the subclones. Synthetic oligonucleotides, synthesized according to standard techniques (Applied biosystems 381 A) were used for the subsequent sequence reactions. The PC/GENE sequence analysis software (Intelligenetics) was used for all the analyses of nucleotide and protein sequences.

Figure 3:
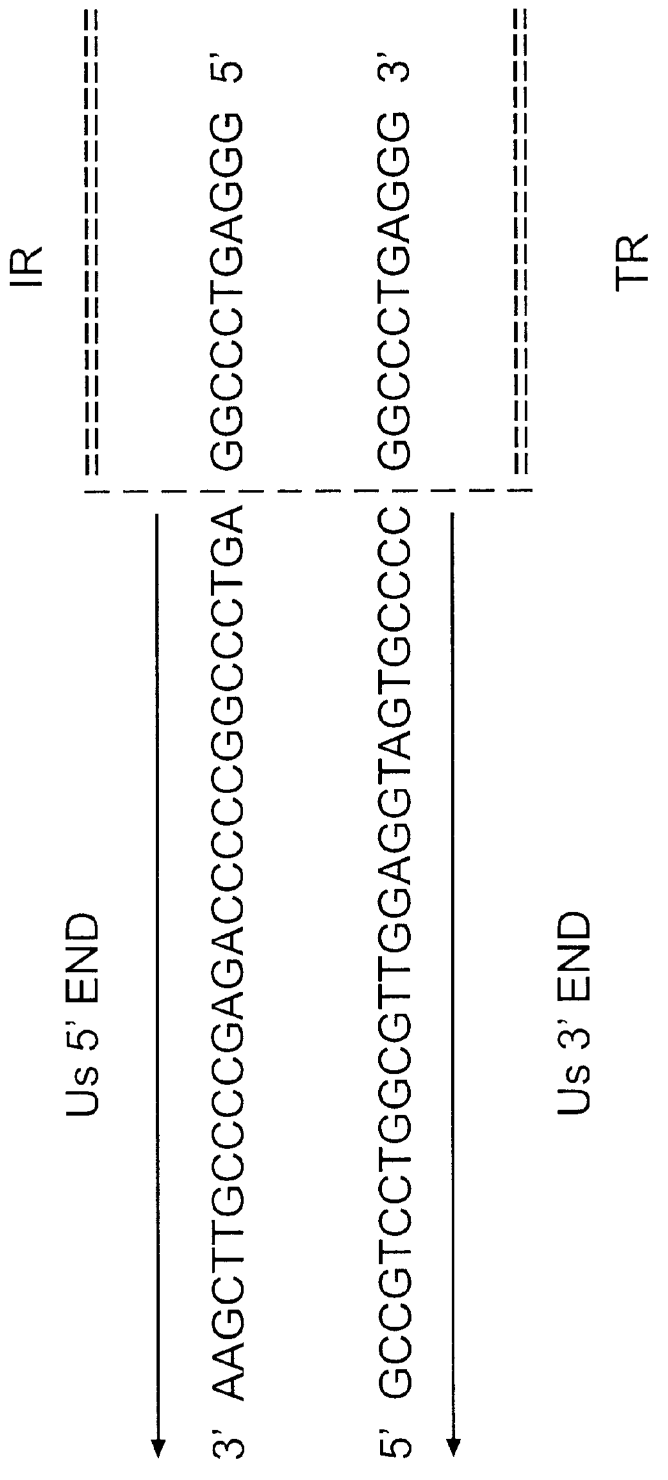
FIG. 3 shows the 5' region (SEQ ID NO:6) and 3' region (SEQ ID NO:7) of the $U_s$ region of BHV-1 ST.

The 4190 bp nucleotide sequence presented in this invention (FIG. 2) is located mainly in the $U_S$ region of the genome of the BHV-1 ST strain but comprises the $U_S$/TR junction and a small part (334 bp) of the terminal repeat region. The $U_S$/repeat regions junction was identified by comparison of the sequences obtained from subclones containing, respectively, the 5' and 3' regions of the BHV-1 ST $U_S$ region (FIG. 3).

It is understood that, relative to the nucleotide sequence of the BHV-1 genomic DNA, natural variations may exist according to the different strains. These variations may be deletions, substitutions, insertions, inversions or additions of one or more nucleotides, which may optionally modify the position of one or more restriction sites, thus producing a restriction map close to that represented in FIG. 1.

The sequence region contains 3 complete open reading frames potentially encoding proteins. The amino acid sequences deduced from these open reading frames are indicated opposite the sequence presented in FIG. 2.

These protein sequences were compared for homology with the proteins encoded by the $U_S$ regions of other alphaherpesviruses. The results of this comparison are presented in Table I.

It appears that the best scores for the first open reading frame are obtained with the "gİ-equivalent" glycoproteins encoded by EHV-1, PRV and HSV-1; this first open reading frame was therefore designated BHV-1 gİ. The best scores for the second open reading frame are obtained with the "gE-equivalent" glycoproteins encoded by EHV-1, PRV and HSV-1; this second open reading frame was therefore designated BHV-1 gE. Finally, the best scores for the third open reading frame are obtained with the "US9-equivalent" proteins encoded by PRV, VZV and HSV-1; this third open reading frame was therefore designated BHV-1 US9.

EXAMPLE 2

Construction of the deletion plasmid pBHV 008

The plasmid pBHV001 containing the 16.4 kb EcoRI-EcoRI fragment (FIG. 1) was digested with EcoRI and HindIII in order to liberate the HindIII-EcoRI fragment of about 4.4 kb. This fragment was cloned into the pBluescript SK+ vector, previously digested with EcoRI and HindIII in order to generate the plasmid pBHV003.

The plasmid pBHV003 was digested with SauI, repaired with Klenow polymerase, then digested with PstI in order to release the 1.1 kb blunt-ended PstI fragment which was then cloned into the pBluescript SK+ vector, previously digested with PstI and SmaI, in order to generate the plasmid pBHV005 containing the flanking 3' region of the deletion plasmid.

The plasmid pBHV001 was digested with HindIII in order to liberate the 7.5 kb HindIII-HindIII fragment (FIG. 1). This fragment was cloned into the pBluescript SK+ vector previously digested with HindIII and treated with alkaline phosphatase in order to generate the plasmid pBHV004.

The plasmid pBHV004 was digested with PstI in order to obtain a 3.8 kb fragment which was cloned into the PstI site of pBluescript SK+ in order to generate the plasmid BHV006. The plasmid pBHV006 was digested with XhoI, repaired with Klenow polymerase, and digested with SpeI in order finally to release a 2.1 kb blunt-ended SpeI fragment. This fragment was then cloned into the plasmid pBHV005 previously digested with NotI, repaired with Klenow polymerase, and digested by SpeI in order to generate the plasmid pBHV 007 which contains a deletion stretching from nucleotide 430 to nucleotide 3861 on the sequence presented in FIG. 2.

In order to facilitate the work of isolating and purifying the recombinant virus, a cassette for expression of the Eco gpt gene, placed under the control of the SV40 early promoter, was inserted at the level of the deletion. This expression cassette is given here only as an example of a marker which can be used to detect the deleted recombinants. Persons skilled in the art will recognize that there are numerous other examples of genes which can be used as tracers and we are not limiting this part of the invention to a single type of tracer gene or to a single type of promoter for controlling the expression of this tracer gene. Briefly, the plasmid pMAM (Clontech) was digested with BamHI in order to release the SV40 cassette Eco gpt contained in this plasmid. This cassette was then cloned into the plasmid pBHV007, previously digested with BamHI, in order to generate the plasmid pBHV008 which contains the expression cassette Eco gpt in place of the deletion previously described, flanked in 5' and 3' by the flanking sequences necessary for the homologous recombination in the US region of the BHV-1 ST virus genome.

EXAMPLE 3

Construction of the deletion plasmids pBHV010 and pBHV011

The plasmid pBHV003 was digested with PvuI, treated with Klenow polymerase, and digested with HindIII in order to liberate the 3 kb Hind III fragment (blunt ended).

This fragment was cloned into a vector pBR322 mutated at the level of the unique SalI restriction site and digested with EcoRV and HindIII in order to generate the plasmid pBHV009. The plasmid pBHV009 was digested with SalI in order to delete the 840 bp SalI-SalI fragment (positions 873→1713 in the sequence of FIG. 2) and isolate the 6360 bp SalI-SalI fragment (fragment A). The plasmid pSVβ (Clontech) containing an SV40-lacZ cassette was digested with EcoRI and SalI in order to liberate the 3855 bp EcoRI-SalI fragment (SV40-lacZ cassette (fragment B). The fragments A and B were then repaired with Klenow polymerase and ligated together in order to generate the plasmids pBHV010 and pBHV011 which correspond, respectively, to the right and left orientations of the SV40-lacZ cassette relative to the flanking BHV-1 sequences.

EXAMPLE 4

Production of BHV-1 recombinants deleted in gİ, gE and US9

A. Transfections

All the transfection experiments were carried out according to a standard calcium phosphate precipitation technique ("calcium phosphate transfection system" kit marketed by Gibco-BRL). The precipitate produced with 5 μg of viral DNA and a variable quantity of plasmid DNA (pBHV008) (5 to 20 μg) with the aid of the kit is gently added to IPB3 cells which have been in culture for 24 hours in a 25-$cm^2$ bottle After one night at 37° C., the cells are rinsed with serum-free medium, then incubated in 1% FCS DMEM until a CPE appears. When the latter is generalized, the cotransfection supernatant is aliquoted and stored at −80° C.

The cotransfection can also be carried out with the aid of other techniques known to persons skilled in the art, in particular according to the liposome technique, performed with the Gibco-BRL "lipofectin" kit.

B. Isolation and purification of the recombinant viruses

The isolation and purification of the recombinant viruses were carried out according to the cloning technique under agarose described below. RV cells are cultured in Petri dishes (Corning 4.5 cm in diameter) in DMEM medium containing 10% FCS until the cellular lawns are well established. The culture medium is then removed and 1 ml of supernatant, derived from the transfection previously described, and diluted so as to obtain isolated plaques, is adsorbed onto the cells for 1 hour at 37° C. The transfection supernatant is removed and replaced with 5 ml of DMEM medium containing 1% agarose, maintained under superfusion at 37° C. When the agarose is solidified, the dishes are incubated for 48 to 72 hours at 37° C. in a $CO_2$ incubator until plaques appear. The plaques, spotted with the naked eye or under a microscope, are collected through the agarose with the aid of a micropipette and each sample, after dissociation in DMEM medium, is placed in culture in a well, containing RV cells established in a lawn and cultured in 10% FCS DMEM, in a 96-well plate (Falcon).

Once amplified, the progeny of each plaque is analyzed using the culture supernatant from each well. Half the volume of each supernatant is analyzed according to a standard dot blot technique with an Eco gpt probe or with the appropriate probe if another tracer gene is used. The other half of the supernatant is stored at −80° C. and serves, after sonication, for a new cloning cycle under agarose, in Petri dishes, as previously described. The recombinant virus was purified by 4 successive cloning/hybridization cycles and designated BHV-1 A11.

When the transfection is performed with an insertion plasmid containing an SV40-lacZ expression casstette (insertion plasmids pBHV010 or pBHV011), the detection and isolation of the recombinants is performed as follows.

The transfection step is performed as previously described. The transfection supernatant is removed and replaced with 5 ml of DMEM medium containing 1% agarose. When the agarose is solidified, the dishes are incubated 48 to 72 hours at 37° C. in a $CO_2$ incubator, until plaques appear. There is then added over the agar a solution of X-gal (500 μg/ml) in DMEM medium containing 1% agarose, maintained under superfusion at 37° C. The Petri dishes are then incubated at 37° C. in a $CO_2$ incubator for 3 to 4 hours and the blue plaques are collected through the agarose with the aid of a micropipette. Each plaque collected is dissociated in DMEM medium and dilutions of each plaque are adsorbed as above on RV cells. Four purification cycles are necessary in order to obtain a recombinant virus at 100% purity.

C. Southern blot analysis of the DNA from BHV-1 A11 recombinant

Figure 4A:
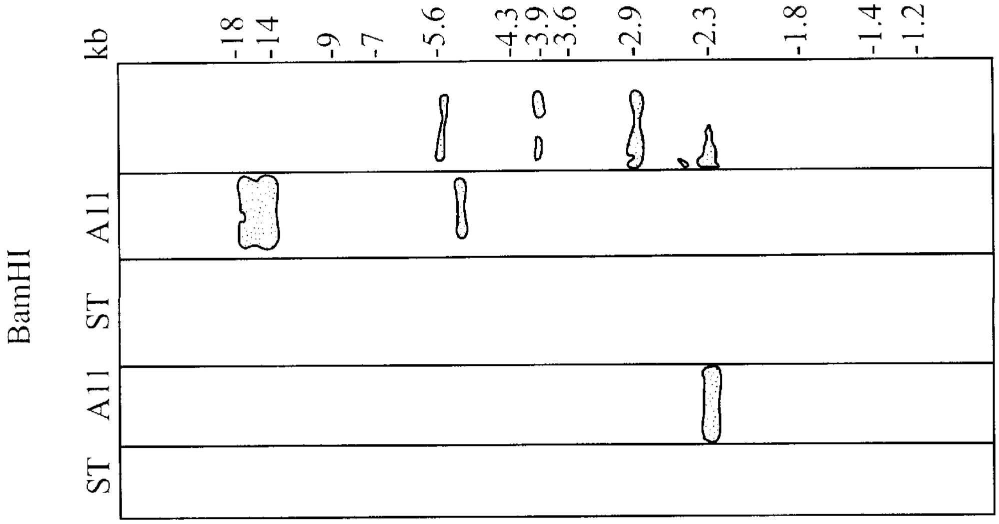
FIGS. 4*a*, 4*b* and 4*c* show Southern blot analysis of the DNA from BHV-1 A11 recombinant.
Figure 4B:
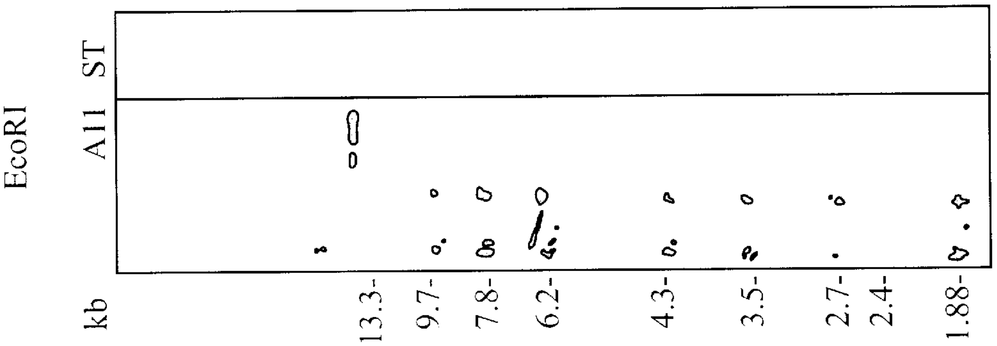
Figure 4C:
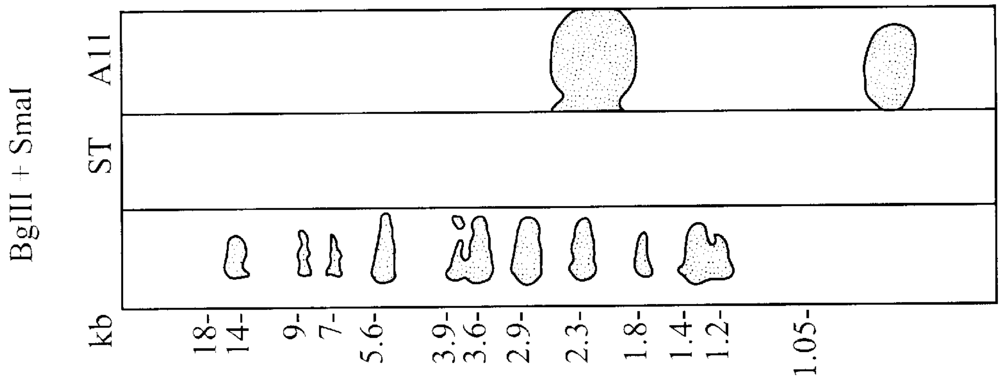

In order to study if the recombination occurred in a homologous manner on the $U_S$ fragment of BHV-1, the DNA from the recombinant virus "A 11" was analyzed by Southern blotting (FIGS. 4*a*, 4*b* and 4*c*). The blots were probed with the 2.1 kb BamHI-BamHI fragment, which corresponds to the SV40-Eco gpt cassette inserted in the deletion plasmid, and with the 2.9 kb pBluescript vector. For each blot, the DNA from the parental virus BHV-1 ST and the DNA from the recombinant virus BHV-1 A11 (1 μg of each sample) were digested with the following enzymes before being loaded onto the gel: BamHI, EcoRI, HindIII, BglII+SmaI. A control consisting of uninfected cells was included in each blot.

The results of these hybridizations have shown that the recombination had effectively occurred at the level of the site chosen.

The Eco gpt probe hybridizes with a 2.1 kb BamHI fragment, which indicates that the SV40-Eco gpt cassette was integrated into the genome of the virus A 11. It hybridizes with a 15 kb EcoRI fragment, which corresponds to the size of the 16.4 kb EcoRI fragment, deleted by 3.5 kb, and having inserted the 2.1 kb SV40-Eco gpt cassette. It also hybridizes with 18 kb, 14 kb and 5.2 kb HindIII fragments, which indicates that the recombination indeed took place at the chosen site and that the two isomeric forms of the recombinant genome are present. Finally, it hybridizes with two BglII-SmaI fragments of 2.3 kb and 0.7 kb, which correspond to the theoretical sizes expected in the recombinant virus.

The pBluescript probe does not hybridize with any BamHI, EcoRI, HindIII or BglII+SmaI fragment of the recombinant virus A 11, which indicates that the recombination occurred without integration of sequences of the vector into the virus genome (not shown).

EXAMPLE 5

Cloning and expression of the BHV-1 gE glycoprotein in a baculovirus vector

A. Materials

The plasmid pBHV001 served as source of DNA for isolating the BHV-1 gE gene. The plasmid pAcRP23 was used to construct the recombination plasmid (Luckow V. A. and Summers M. D., Virology, 170, 31–99, 1989). The baculovirus *Autographa californica* Ac NPV (Summers M. D. and Smith G. E., A manual of methods for baculovirus vectors and insect cell culture procedures, Texas Agricultural Experimental Station bulletin No. 1555. Texas Agricultural Experimental Station, College Station, Tex.) was used as parental virus for the recombination experiments. The Sf 21 cell line (cells derived from *Spodoptera frugiperda*) was used for the cultures of parental virus and of the recombinant viruses. The cells were cultured in TC100 medium (Flow Labs).

B. Construction of the recombination plasmid pIL003

The 840 bp SalI-SalI fragment (coordinates 873–1713 on the sequence of FIG. 2) was cloned into the vector M13 mp18 and mutagenized by the Eckstein method (Eckstein F. et al.,f Nucl. Acids Res., 16, 791–802, 1988) with the oligonucleotide IL001 (SEQ ID No. 5: 5' GGCATTTGGATCCAATGCAACCCAC 3') in order to introduce a BamHI site just upstream of the ATG of the BHV-1 gE gene. The mutated fragment was digested with SalI and BamHI in order to liberate a 120 bp BamHI-SalI fragment (fragment A). The plasmid pBHV001, containing the the 16.4 kb EcoRI BHV-1 fragment, was digested with SalI and AsuII in order to liberate the 1715 bp SalI-AsuII fragment (coordinates 1713→3425 on the sequence of FIG. 2). This fragment was then digested with HindIII in order to obtain the 1000 bp SalI-HindIII (fragment B) and 715 bp HindIII-AsuII (fragment C) fragments. The fragments A and B were ligated into the pBluescript SK+ vector previously digested with BamHI and HindIII in order to generate the plasmid pIL001. The fragment C and a synthetic adaptor AsuII-EcoRV-BamHI were ligated into the pBluescript SK+ vector previously digested with BamHI and HindIII in order to generate the plasmid pIL002. The plasmid pIL001 was digested with BamHI and HindIII in order to liberate the 1100 bp BamHI-HindIII fragment (fragment D). The plasmid pIL002 was digested with BamHI and HindIII in order to liberate the 730 bp BamHI-HindIII fragment (fragment E). The fragments D and E were then ligated into the vector pAcRP23, previously digested with BamHI and treated with alkaline phosphatases in order to generate the plasmid pIL003. The plasmid pIL003 contains the BHV-1 gE gene under the control of the promoter of the polyhedrin gene and the flanking 5' and 3' sequences permitting homologous recombination in *Autographa californica* Ac NPV.

C. Transfection

The baculovirus recombinants were generated by cotransfection of 1 μg Ac NPV DNA and 2 μg of pIL003 DNA into *S. frugiperda* cells according to the calcium phosphate precipitation technique. After 4 hours of contact at room temperature, the cells were rinsed with TC100 medium and cultured for 3 days at 28° C. The supernatants were then recovered in order to be inoculated into the Petri dishes which will serve for the isolation of the recombinants.

D. Isolation and purification of the recombinant virus

Dilutions of the cotransfection supernatant are adsorbed for 1 hour at room temperature onto Sf21 cells cultured in Petri dishes. The supernatant is then removed and replaced with culture medium containing 2% agarose in superfusion. When the agar is solidified 1 ml of medium is added over the agar layer, and the cells are incubated at 28° C. for 3 to 4 days. The Petri dishes are then stained with neutral red for 1 hour. The polyhedrin-negative plaques are collected with a micropipette, mixed with culture medium and vortexed. Dilutions of each plaque are then prepared and adsorbed as above onto *S. frugiperda* cells. Three purification cycles were performed in order to obtain a recombinant virus at 100% purity.

The recombinant baculovirus obtained from the transfection with the plasmid pIL003 was designated rBAC001.

The invention which has just been described can be the subject of numerous variants spontaneously accessible to a person skilled in the art.

Thus, instead of cloning the insertion region by the process described, it is possible to locate it by hybridization or to amplify it by means of probes manufactured in a conventional manner from the nucleotide sequences SEQ ID No.:1 or 5 and then to insert it into the usual plasmids or vectors, for example in the case where there is used as starting material a natural BHV strain containing variations in the restriction sites used.

Likewise, the insertion region according to the invention encompasses all the variants of natural origin or otherwise, which continue to allow a person skilled in the art to perform the deletions or insertions according to the invention.

TABLE I

| BHV-1 protein encoded by the gene | Size | Homologous size encoded by the gene | Size | % homology |
|---|---|---|---|---|
| gI | 380 aa | EVH-1 gI | 413 aa | 45.4% |
| | | PRV gp63 | 350 aa | 42.6% |
| | | HSV-1 gI | 390 aa | 37.9% |
| | | VZV gpIV | 354 aa | 32.5% |
| qE | 575 aa | EHV-1 gE | 552 aa | 46.7% |
| | | PRV gI | 577 aa | 38.5% |

TABLE I-continued

| BHV-1 protein encoded by the gene | Size | Homologous size encoded by the gene | Size | % homology |
|---|---|---|---|---|
| | | HSV-1 gE | 550 aa | 38.4% |
| | | VZH gpI | 623 aa | 36.2% |
| US9 | 158 aa | PRV 11K | 106 aa | 54.7% |
| | | HSV-1 US9 | 90 aa | 50.0% |
| | | VZV VP65 | 102 aa | 46.1% |

We claim:

1. A method of producing a bovine herpesvirus type 1 (BHV-1) gE protein comprising:

culturing a recombinant baculovirus comprising a DNA fragment consisting essentially of nucleotides 1594 to 3318 of SEQ ID NO:1; and isolating the protein from said baculovirus.

* * * * *

UNITED STATES PATENT AND TRADEMARK OFFICE

CERTIFICATE OF CORRECTION

PATENT NO. : 6,224,878 B1
DATED : May 1, 2001
INVENTOR(S) : Leung-Tack et al.

It is certified that error appears in the above-identified patent and that said Letters Patent is hereby corrected as shown below:

Title page,
Item [73], Assignee, Merial, Lyon (FR)

Item [63], Continuation of application No. 08,199,172 filed as application No. PCT/FR93/00642 on June 25, 1993, now abandoned.

Item [30], Foreign Application Priority Data
June 26, 1992 (FR) ...............................................92 07930

Signed and Sealed this

Twenty-fifth Day of December, 2001

*Attest:*

JAMES E. ROGAN
*Director of the United States Patent and Trademark Office*

*Attesting Officer*

SEQUENCE LISTING

```
(1) GENERAL INFORMATION:

   (iii) NUMBER OF SEQUENCES: 7


(2) INFORMATION FOR SEQ ID NO: 1:

     (i) SEQUENCE CHARACTERISTICS:
          (A) LENGTH: 4190 base pairs
          (B) TYPE: nucleic acid
          (C) STRANDEDNESS: double
          (D) TOPOLOGY: linear

    (ii) MOLECULE TYPE: DNA (genomic)

   (iii) HYPOTHETICAL: NO

   (iii) ANTI-SENSE: NO

    (vi) ORIGINAL SOURCE:
          (A) ORGANISM: Type 1 Bovine Herpesvirus
          (B) STRAIN: ST

    (ix) FEATURE:
          (A) NAME/KEY: CDS
          (B) LOCATION: 172..1311
          (D) OTHER INFORMATION: /function= "envelope glycoprotein"
               /product= "glycoprotein gI"
               /standard_name= "BHV-1 gI"

    (ix) FEATURE:
          (A) NAME/KEY: CDS
          (B) LOCATION: 1594..3318
          (D) OTHER INFORMATION: /function= "envelop glycoprotein"
               /product= "glycoprotein gE"
               /standard_name= "BHV-1 gE"

    (ix) FEATURE:
          (A) NAME/KEY: CDS
          (B) LOCATION: 3388..3861
          (D) OTHER INFORMATION: /product= "protein US9"
               /standard_name= "BHV US9"

    (xi) SEQUENCE DESCRIPTION: SEQ ID NO: 1:

TTTGGCAACG TCAACTACAG CGCGCTGCCC GGGTGAGCGG CCTAGGCCCT CCCCCGACCG      60

CCCCCTTTGC TCCTAGCCCC CGGCTCCAGC CGAGCCGCGC GGGGCGGAGA TAAAGCGCCC     120

GCGTCGGCGA CTCAAGCCAT TGCCGCGACC TTGTCCTCCG GCGCGCTCGC G ATG CGG      177
                                                          Met Arg
                                                            1

TGC CTG TTG CTC TGG ATG GTG GTG CTG GCC GCG CGA GCG GCG CCC GCT       225
Cys Leu Leu Leu Trp Met Val Val Leu Ala Ala Arg Ala Ala Pro Ala
          5                  10                  15
```

-continued

```
CGC AGC CTT GTG TAT CGC GGC GAG GCA GTC GGC CTG CGC GCG GAC GGC      273
Arg Ser Leu Val Tyr Arg Gly Glu Ala Val Gly Leu Arg Ala Asp Gly
     20                  25                  30

CCC GTA GCG TTC GCT GTC CAC CCG ACC GAC GCA ACG CTC GCG CTG CGG      321
Pro Val Ala Phe Ala Val His Pro Thr Asp Ala Thr Leu Ala Leu Arg
 35                  40                  45                  50

GGC CGG CTG ATT TTC CTG GAA CAC CAG CTC CCG GCC GGG CGG CGC TAC      369
Gly Arg Leu Ile Phe Leu Glu His Gln Leu Pro Ala Gly Arg Arg Tyr
                 55                  60                  65

AAC GGG ACC GTC GAG CTG CTG CGC TAC CAC GCC GCG GGC GAC TGC TTC      417
Asn Gly Thr Val Glu Leu Leu Arg Tyr His Ala Ala Gly Asp Cys Phe
             70                  75                  80

GTT ATG CTG CAG ACG ACC GCG TTC GCC TCC TGC CCG CGC GTC GCG AAC      465
Val Met Leu Gln Thr Thr Ala Phe Ala Ser Cys Pro Arg Val Ala Asn
         85                  90                  95

AAC GCC TTT CGC TCC TGC CTG CAC GCC GAC ACG CGC CCC GCT CGC AGC      513
Asn Ala Phe Arg Ser Cys Leu His Ala Asp Thr Arg Pro Ala Arg Ser
    100                 105                 110

GAG CGG CGC GCG AGC GCC GCG GTC GAA AAC CAC GTG CTC TTC TCC ATC      561
Glu Arg Arg Ala Ser Ala Ala Val Glu Asn His Val Leu Phe Ser Ile
115                 120                 125                 130

GCC CGT CCG CGC CCA ATA GAC TCG GGG CTC TAC TTT CTG CGC GTC GGC      609
Ala Arg Pro Arg Pro Ile Asp Ser Gly Leu Tyr Phe Leu Arg Val Gly
                135                 140                 145

ATC TAC GGC GGC ACC GCG GGC AGC GAG CGC CGC CGA GAC GTC TTT CCC      657
Ile Tyr Gly Gly Thr Ala Gly Ser Glu Arg Arg Arg Asp Val Phe Pro
            150                 155                 160

TTG GCC GCG TTT GTA CAC AGC TTC GGT GAG CCC GGA GAC CCA GAG GCC      705
Leu Ala Ala Phe Val His Ser Phe Gly Glu Pro Gly Asp Pro Glu Ala
        165                 170                 175

GCG GCG CGC ACC CCG GCA CCG TCG AGG CAG TCG AGG CCC GCT GCG AGC      753
Ala Ala Arg Thr Pro Ala Pro Ser Arg Gln Ser Arg Pro Ala Ala Ser
    180                 185                 190

GGC CTG ACC AGC TCG GCG AGC CTC TAC GAC CGC GCG CTG GCG CGT TCC      801
Gly Leu Thr Ser Ser Ala Ser Leu Tyr Asp Arg Ala Leu Ala Arg Ser
195                 200                 205                 210

CCG CAG GCG CCG CCA CCA CGC CCG GCC CCA CCG CGA GCA GCG AGA GCG      849
Pro Gln Ala Pro Pro Pro Arg Pro Ala Pro Pro Arg Ala Ala Arg Ala
                215                 220                 225

GGG CCG CGA CGC CCA GAG AGG GTC GAC GAG ACG ACG GAA GTC GAG GCC      897
Gly Pro Arg Arg Pro Glu Arg Val Asp Glu Thr Thr Glu Val Glu Ala
            230                 235                 240

GCG ACG AGA GCG GGC TCG GCG TTT GCC CTC ACC ACG CCC CCG GCC GGC      945
Ala Thr Arg Ala Gly Ser Ala Phe Ala Leu Thr Thr Pro Pro Ala Gly
        245                 250                 255

CCG ACC GCC AGC CCC GCC GCC AGC CCC TCC CGT GCC TTT AGC GCG GCC      993
Pro Thr Ala Ser Pro Ala Ala Ser Pro Ser Arg Ala Phe Ser Ala Ala
    260                 265                 270

GCC CCG GCC GCC GCT GCG CAG CCG GCC GGA GAC ACG CCC GCT CGC TTC     1041
Ala Pro Ala Ala Ala Ala Gln Pro Ala Gly Asp Thr Pro Ala Arg Phe
275                 280                 285                 290

CGG CGC CAA CTG GCG TCG ATC CTA GTG CCT CTG TGC GTG CTG GTG CTG     1089
Arg Arg Gln Leu Ala Ser Ile Leu Val Pro Leu Cys Val Leu Val Leu
                295                 300                 305

CTG CTG CTT GCG CTC TGC GCC GCG ACG GTA AAC TGC GCG CTG CGC CGT     1137
Leu Leu Leu Ala Leu Cys Ala Ala Thr Val Asn Cys Ala Leu Arg Arg
            310                 315                 320

CGC CTG CTG CCG TGC TCT CGG CGC GTT TAC AAG CCG CGG ACG TGC GCG     1185
Arg Leu Leu Pro Cys Ser Arg Arg Val Tyr Lys Pro Arg Thr Cys Ala
        325                 330                 335
```

-continued

```
GCG TGC GGG AGC GGC ACT TGC GCG GGG CGG CCC CCC TGC CGC GGC GCG     1233
Ala Cys Gly Ser Gly Thr Cys Ala Gly Arg Pro Pro Cys Arg Gly Ala
    340                 345                 350

GCA CCG AGC GCC CCA GCC ACC GTC GTG GCA CTG GGC TCC CGG CCA AAG     1281
Ala Pro Ser Ala Pro Ala Thr Val Val Ala Leu Gly Ser Arg Pro Lys
355                 360                 365                 370

GCG CCC CCC CTC GCC ACC ATC AGC GAA GAA TAAACGCCGC GCGCGGCAAA       1331
Ala Pro Pro Leu Ala Thr Ile Ser Glu Glu
                375                 380

CGATCTCGCT CGCGTGTGTC TTGGTTTCTG CGCGGCGGGC GGGGTGGGGA GCGGGCAAAG   1391

CGGAGGAAGA CCGGGGGCAG GAGCTGCGTG GAGGGCGGAG CCGTTGAGCG GCCCGACCGC   1451

CGCCGGGTTG TTAAATGGGT CTCGCGCGGC TCGTGGTTCC ACACTGCGCC GGAGAACCAG   1511

CGCGACGTTC GCTGCGTGTG GAACCACGAG CTGCGTTCCG GGAACGGCGG CACGCGAGAG   1571

GGTTCGAAAA GGGCATTTGG CA ATG CAA CCC ACC GCG CCG CCC CGG CGG CGG    1623
                         Met Gln Pro Thr Ala Pro Pro Arg Arg Arg
                           1               5                  10

TTG CTG CCG CTG CTG CTG CCG CAG CTA TTG CTT TTC GGG CTG ATG GCC     1671
Leu Leu Pro Leu Leu Leu Pro Gln Leu Leu Leu Phe Gly Leu Met Ala
                 15                  20                  25

GAG GCC GAG CCC GCG ACC GAA ACC CCG GGC TCG GCT TCG GTC GAC ACG     1719
Glu Ala Glu Pro Ala Thr Glu Thr Pro Gly Ser Ala Ser Val Asp Thr
             30                  35                  40

GTC TTC ACG GCG CGC GCC GGC GCG CCC GTC TTT CTC CCA GGG CCC GCG     1767
Val Phe Thr Ala Arg Ala Gly Ala Pro Val Phe Leu Pro Gly Pro Ala
         45                  50                  55

GCG CGC CCG GAC GTG CGC GCC GTT CGC GGC TGG AGC GTC CTC GCG GGC     1815
Ala Arg Pro Asp Val Arg Ala Val Arg Gly Trp Ser Val Leu Ala Gly
     60                  65                  70

GCC TGC TCG CCG CCC GTG CCG GAG CCC GTC TGC CTC GAC GAC CGC GAG     1863
Ala Cys Ser Pro Pro Val Pro Glu Pro Val Cys Leu Asp Asp Arg Glu
 75                  80                  85                  90

TGC TTC ACC GAC GTG GCC CTG GAC GCG GCC TGC CTG CGA ACC GCC CGC     1911
Cys Phe Thr Asp Val Ala Leu Asp Ala Ala Cys Leu Arg Thr Ala Arg
                 95                 100                 105

GTG GCC CCG CTG GCC ATC GCG GAG CTC GCC GAG CGG CCC GAC TCG ACG     1959
Val Ala Pro Leu Ala Ile Ala Glu Leu Ala Glu Arg Pro Asp Ser Thr
            110                 115                 120

GGC GAC AAA GAG TTT GTT CTC GCC GAC CCG CAC GTC TCG GCG CAG CTG     2007
Gly Asp Lys Glu Phe Val Leu Ala Asp Pro His Val Ser Ala Gln Leu
        125                 130                 135

GGT CGC AAC GCG ACC GGG GTG CTG ATC GCG GCC GCA GCC GAG GAG GAC     2055
Gly Arg Asn Ala Thr Gly Val Leu Ile Ala Ala Ala Ala Glu Glu Asp
    140                 145                 150

GGC GGC GTG TAC TTC CTG TAC GAC CGG CTC ATC GGC GAC GCC GGC GAC     2103
Gly Gly Val Tyr Phe Leu Tyr Asp Arg Leu Ile Gly Asp Ala Gly Asp
155                 160                 165                 170

GAG GAG ACG CAG TTG GCG CTG ACG CTG CAG GTC GCG ACG GCC GGC GCG     2151
Glu Glu Thr Gln Leu Ala Leu Thr Leu Gln Val Ala Thr Ala Gly Ala
                175                 180                 185

CAG GGC GCC GCG CGG GAC GAG GAG AGG GAA CCA GCG ACC GGG CCC ACC     2199
Gln Gly Ala Ala Arg Asp Glu Glu Arg Glu Pro Ala Thr Gly Pro Thr
            190                 195                 200

CCC GGC CCG CCG CCC CAC CGC ACG ACG ACA CGC GCG CCC CCG CGG CGG     2247
Pro Gly Pro Pro Pro His Arg Thr Thr Thr Arg Ala Pro Pro Arg Arg
        205                 210                 215

CAC GGC GCG CGC TTC CGC GTG CTG CCG TAC CAC TCC CAC GTA TAC ACC     2295
His Gly Ala Arg Phe Arg Val Leu Pro Tyr His Ser His Val Tyr Thr
```

-continued

```
    220                 225                 230

CCG GGC GAT TCC TTT CTG CTA TCG GTG CGT CTG CAG TCT GAG TTT TTC     2343
Pro Gly Asp Ser Phe Leu Leu Ser Val Arg Leu Gln Ser Glu Phe Phe
235                 240                 245                 250

GAC GAG GCT CCC TTC TCG GCC AGC ATC GAC TGG TAC TTC CTG CGG ACG     2391
Asp Glu Ala Pro Phe Ser Ala Ser Ile Asp Trp Tyr Phe Leu Arg Thr
                255                 260                 265

GCC GGC GAC TGC GCG CTC ATC CGC ATA TAC GAG ACG TGC ATC TTC CAC     2439
Ala Gly Asp Cys Ala Leu Ile Arg Ile Tyr Glu Thr Cys Ile Phe His
            270                 275                 280

CCC GAG GCA CCG GCC TGC CTG CAC CCC GCC GAC GCG CAG TGC AGC TTC     2487
Pro Glu Ala Pro Ala Cys Leu His Pro Ala Asp Ala Gln Cys Ser Phe
        285                 290                 295

GCG TCG CCG TAC CGC TCC GAG ACC GTG TAC AGC CGG CTG TAC GAG CAG     2535
Ala Ser Pro Tyr Arg Ser Glu Thr Val Tyr Ser Arg Leu Tyr Glu Gln
    300                 305                 310

TGC CGC CCG GAC CCT GCC GGT CGC TGG CCG CAC GAG TGC GAG GGC GCC     2583
Cys Arg Pro Asp Pro Ala Gly Arg Trp Pro His Glu Cys Glu Gly Ala
315                 320                 325                 330

GCG TAC GCG GCG CCC GTT GCG CAC CTG CGT CCC GCC AAT AAC AGC GTA     2631
Ala Tyr Ala Ala Pro Val Ala His Leu Arg Pro Ala Asn Asn Ser Val
                335                 340                 345

GAC CTG GTC TTT GAC GAC GCG CCG GCT GCG GCC TCC GGG CTT TAC GTC     2679
Asp Leu Val Phe Asp Asp Ala Pro Ala Ala Ala Ser Gly Leu Tyr Val
            350                 355                 360

TTT GTG CTG CAG TAC AAC GGC CAC GTG GAA GCT TGG GAC TAC AGC CTA     2727
Phe Val Leu Gln Tyr Asn Gly His Val Glu Ala Trp Asp Tyr Ser Leu
        365                 370                 375

GTC GTT ACT TCG GAC CGT TTG GTG CGC GCG GTC ACC GAC CAC ACG CGC     2775
Val Val Thr Ser Asp Arg Leu Val Arg Ala Val Thr Asp His Thr Arg
    380                 385                 390

CCC GAG GCC GCA GCC GCC GAC GCT CCC GAG CCA GGC CCA CCG CTC ACC     2823
Pro Glu Ala Ala Ala Ala Asp Ala Pro Glu Pro Gly Pro Pro Leu Thr
395                 400                 405                 410

AGC GAG CCG GCG GGG GCG CCC ACC GGG CCC GCG CCC TGG CTT GTG GTG     2871
Ser Glu Pro Ala Gly Ala Pro Thr Gly Pro Ala Pro Trp Leu Val Val
                415                 420                 425

CTG GTG GGC GCG CTT GGA CTC GCG GGA CTG GTG GGC ATC GCG GCC CTC     2919
Leu Val Gly Ala Leu Gly Leu Ala Gly Leu Val Gly Ile Ala Ala Leu
            430                 435                 440

GCC GTT CGG GTG TGC GCG CGC CGC GCA AGC CAG AAG CGC ACC TAC GAC     2967
Ala Val Arg Val Cys Ala Arg Arg Ala Ser Gln Lys Arg Thr Tyr Asp
        445                 450                 455

ATC CTC AAC CCC TTC GGG CCC GTA TAC ACC AGC TTG CCG ACC AAC GAG     3015
Ile Leu Asn Pro Phe Gly Pro Val Tyr Thr Ser Leu Pro Thr Asn Glu
    460                 465                 470

CCG CTC GAC GTG GTG GTG CCA GTT AGC GAC GAC GAA TTT TCC CTC GAC     3063
Pro Leu Asp Val Val Val Pro Val Ser Asp Asp Glu Phe Ser Leu Asp
475                 480                 485                 490

GAA GAC TCT TTT GCG GAT GAC GAC AGC GAC GAT GAC GGG CCC GCT AGC     3111
Glu Asp Ser Phe Ala Asp Asp Asp Ser Asp Asp Asp Gly Pro Ala Ser
                495                 500                 505

AAC CCC CCT GCG GAT GCC TAC GAC CTC GCC GGC GCC CCA GAG CCA ACT     3159
Asn Pro Pro Ala Asp Ala Tyr Asp Leu Ala Gly Ala Pro Glu Pro Thr
            510                 515                 520

AGC GGG TTT GCG CGA GCC CCC GCC AAC GGC ACG CGC TCG AGT CGC TCT     3207
Ser Gly Phe Ala Arg Ala Pro Ala Asn Gly Thr Arg Ser Ser Arg Ser
        525                 530                 535

GGG TTC AAA GTT TGG TTT AGG GAC CCG CCT GAA GAC GAT GCC GCG CCA     3255
```

-continued

```
Gly Phe Lys Val Trp Phe Arg Asp Pro Pro Glu Asp Asp Ala Ala Pro
    540                 545                 550

GCG CGG GCC CCG GCC GCA CCA GAT TAC ACC GTG GTA GCA GCG CGA CTC     3303
Ala Arg Ala Pro Ala Ala Pro Asp Tyr Thr Val Val Ala Ala Arg Leu
555                 560                 565                 570

AAG TCC ATC CTC CGC TAGGCGCCCC CCCCCGCGCG CGCGCTGTGC CGTCTGACGG     3358
Lys Ser Ile Leu Arg
                575

AAAGCACCCG CGTGTAGGGC TGCATATAA ATG GAG CGC TCA CAC AAA GCC TCG     3411
                                Met Glu Arg Ser His Lys Ala Ser
                                  1               5

TGC GGC TGC TTC GAA GGC ATG GAG AGT CCA CGC AGC GTC GTC AAC GAA     3459
Cys Gly Cys Phe Glu Gly Met Glu Ser Pro Arg Ser Val Val Asn Glu
     10                  15                  20

AAC TAT CGA GGC GCT GAT GAG GCC GAT GCA GCG CCC CCC TCA CCG CCG     3507
Asn Tyr Arg Gly Ala Asp Glu Ala Asp Ala Ala Pro Pro Ser Pro Pro
 25                  30                  35                  40

CCG GAG GGC TCC ATC GTG TCC ATC CCC ATC CTC GAG CTC ACC ATC GAG     3555
Pro Glu Gly Ser Ile Val Ser Ile Pro Ile Leu Glu Leu Thr Ile Glu
                 45                  50                  55

GAC GCG CCG GCC AGC GCA GAA GCA ACC GGC ACC GCG GCA GCC GCA CCC     3603
Asp Ala Pro Ala Ser Ala Glu Ala Thr Gly Thr Ala Ala Ala Ala Pro
             60                  65                  70

GCT GGG CGC ACG CCA GAC GCG AAC GCA GCA CCC GGC GGC TAC GTG CCA     3651
Ala Gly Arg Thr Pro Asp Ala Asn Ala Ala Pro Gly Gly Tyr Val Pro
         75                  80                  85

GTT CCC GCG GCG GAT GCG GAC TGC TAT TAT AGC GAA AGC GAC AGC GAG     3699
Val Pro Ala Ala Asp Ala Asp Cys Tyr Tyr Ser Glu Ser Asp Ser Glu
     90                  95                 100

ACG GCA GGC GAG TTT TTG ATA CGC ATG GGG CGG CAG CAG CGG CGG CGG     3747
Thr Ala Gly Glu Phe Leu Ile Arg Met Gly Arg Gln Gln Arg Arg Arg
105                 110                 115                 120

CAT CGG CGG CGG CGC TGC ATG ATA GCA GCG GCC CTG ACT TGC ATT GGC     3795
His Arg Arg Arg Arg Cys Met Ile Ala Ala Ala Leu Thr Cys Ile Gly
                125                 130                 135

CTC GGG GCC TGC GCG GCG GCG GCA GCG GCA GGC GCC GTC CTG GCG TTG     3843
Leu Gly Ala Cys Ala Ala Ala Ala Ala Ala Gly Ala Val Leu Ala Leu
            140                 145                 150

GAG GTA GTG CCC CGG CCC TGAGGCGGGG CCCGACTGTC CCCCTCCCCC            3891
Glu Val Val Pro Arg Pro
        155

CTCCCCCCGT CCGCCCCCCG TCCGCCCGCG AGTAAAGGCT GTCTAATTTT TTCCGCACGC   3951

CCGCGCCTGT CTTTTTTGTG AGGGGAAGAG GGGAGGGCGG GGAAGAGGGG AAGGAGGGGA   4011

AGAGGCGCCA AGCGGCGAGC CGCCGGTCCC GCCGAATGGG TCCGGGCTCG ATAGGCATAC   4071

CGGATGCTTG CGGCTGGCCG GTGCGCTGGA CGACCCAGGC GAAGGAGGGG AAGGAGGGGA   4131

AGAGGGGATT CGGGCCGGCC GCAGCGAGCG GTCAAAGCTC CGGCTCCCCC CTCCCCTCC    4190
```

(2) INFORMATION FOR SEQ ID NO: 2:

(i) SEQUENCE CHARACTERISTICS:
(A) LENGTH: 380 amino acids
(B) TYPE: amino acid
(D) TOPOLOGY: linear (ii) MOLECULE TYPE: protein (xi) SEQUENCE DESCRIPTION: SEQ ID NO: 2:

```
Met Arg Cys Leu Leu Leu Trp Met Val Val Leu Ala Ala Arg Ala Ala
  1               5                  10                  15
```

-continued

```
Pro Ala Arg Ser Leu Val Tyr Arg Gly Glu Ala Val Gly Leu Arg Ala
            20                  25                  30

Asp Gly Pro Val Ala Phe Ala Val His Pro Thr Asp Ala Thr Leu Ala
        35                  40                  45

Leu Arg Gly Arg Leu Ile Phe Leu Glu His Gln Leu Pro Ala Gly Arg
    50                  55                  60

Arg Tyr Asn Gly Thr Val Glu Leu Leu Arg Tyr His Ala Ala Gly Asp
65                  70                  75                  80

Cys Phe Val Met Leu Gln Thr Thr Ala Phe Ala Ser Cys Pro Arg Val
                85                  90                  95

Ala Asn Asn Ala Phe Arg Ser Cys Leu His Ala Asp Thr Arg Pro Ala
            100                 105                 110

Arg Ser Glu Arg Arg Ala Ser Ala Ala Val Glu Asn His Val Leu Phe
        115                 120                 125

Ser Ile Ala Arg Pro Arg Pro Ile Asp Ser Gly Leu Tyr Phe Leu Arg
    130                 135                 140

Val Gly Ile Tyr Gly Gly Thr Ala Gly Ser Glu Arg Arg Arg Asp Val
145                 150                 155                 160

Phe Pro Leu Ala Ala Phe Val His Ser Phe Gly Glu Pro Gly Asp Pro
                165                 170                 175

Glu Ala Ala Ala Arg Thr Pro Ala Pro Ser Arg Gln Ser Arg Pro Ala
            180                 185                 190

Ala Ser Gly Leu Thr Ser Ser Ala Ser Leu Tyr Asp Arg Ala Leu Ala
        195                 200                 205

Arg Ser Pro Gln Ala Pro Pro Pro Arg Pro Ala Pro Pro Arg Ala Ala
    210                 215                 220

Arg Ala Gly Pro Arg Arg Pro Glu Arg Val Asp Glu Thr Thr Glu Val
225                 230                 235                 240

Glu Ala Ala Thr Arg Ala Gly Ser Ala Phe Ala Leu Thr Thr Pro Pro
                245                 250                 255

Ala Gly Pro Thr Ala Ser Pro Ala Ala Ser Pro Ser Arg Ala Phe Ser
            260                 265                 270

Ala Ala Ala Pro Ala Ala Ala Ala Gln Pro Ala Gly Asp Thr Pro Ala
        275                 280                 285

Arg Phe Arg Arg Gln Leu Ala Ser Ile Leu Val Pro Leu Cys Val Leu
    290                 295                 300

Val Leu Leu Leu Leu Ala Leu Cys Ala Ala Thr Val Asn Cys Ala Leu
305                 310                 315                 320

Arg Arg Arg Leu Leu Pro Cys Ser Arg Arg Val Tyr Lys Pro Arg Thr
                325                 330                 335

Cys Ala Ala Cys Gly Ser Gly Thr Cys Ala Gly Arg Pro Pro Cys Arg
            340                 345                 350

Gly Ala Ala Pro Ser Ala Pro Ala Thr Val Val Ala Leu Gly Ser Arg
        355                 360                 365

Pro Lys Ala Pro Pro Leu Ala Thr Ile Ser Glu Glu
    370                 375                 380
```

(2) INFORMATION FOR SEQ ID NO: 3:

(i) SEQUENCE CHARACTERISTICS:
(A) LENGTH: 575 amino acids
(B) TYPE: amino acid
(D) TOPOLOGY: linear (ii) MOLECULE TYPE: protein -continued (xi) SEQUENCE DESCRIPTION: SEQ ID NO: 3:

```
Met Gln Pro Thr Ala Pro Pro Arg Arg Arg Leu Leu Pro Leu Leu Leu
  1               5                  10                  15

Pro Gln Leu Leu Leu Phe Gly Leu Met Ala Glu Ala Glu Pro Ala Thr
             20                  25                  30

Glu Thr Pro Gly Ser Ala Ser Val Asp Thr Val Phe Thr Ala Arg Ala
         35                  40                  45

Gly Ala Pro Val Phe Leu Pro Gly Pro Ala Ala Arg Pro Asp Val Arg
     50                  55                  60

Ala Val Arg Gly Trp Ser Val Leu Ala Gly Ala Cys Ser Pro Pro Val
 65                  70                  75                  80

Pro Glu Pro Val Cys Leu Asp Asp Arg Glu Cys Phe Thr Asp Val Ala
                 85                  90                  95

Leu Asp Ala Ala Cys Leu Arg Thr Ala Arg Val Ala Pro Leu Ala Ile
            100                 105                 110

Ala Glu Leu Ala Glu Arg Pro Asp Ser Thr Gly Asp Lys Glu Phe Val
        115                 120                 125

Leu Ala Asp Pro His Val Ser Ala Gln Leu Gly Arg Asn Ala Thr Gly
    130                 135                 140

Val Leu Ile Ala Ala Ala Ala Glu Glu Asp Gly Gly Val Tyr Phe Leu
145                 150                 155                 160

Tyr Asp Arg Leu Ile Gly Asp Ala Gly Asp Glu Glu Thr Gln Leu Ala
                165                 170                 175

Leu Thr Leu Gln Val Ala Thr Ala Gly Ala Gln Gly Ala Ala Arg Asp
            180                 185                 190

Glu Glu Arg Glu Pro Ala Thr Gly Pro Thr Pro Gly Pro Pro Pro His
        195                 200                 205

Arg Thr Thr Thr Arg Ala Pro Pro Arg Arg His Gly Ala Arg Phe Arg
    210                 215                 220

Val Leu Pro Tyr His Ser His Val Tyr Thr Pro Gly Asp Ser Phe Leu
225                 230                 235                 240

Leu Ser Val Arg Leu Gln Ser Glu Phe Phe Asp Glu Ala Pro Phe Ser
                245                 250                 255

Ala Ser Ile Asp Trp Tyr Phe Leu Arg Thr Ala Gly Asp Cys Ala Leu
            260                 265                 270

Ile Arg Ile Tyr Glu Thr Cys Ile Phe His Pro Glu Ala Pro Ala Cys
        275                 280                 285

Leu His Pro Ala Asp Ala Gln Cys Ser Phe Ala Ser Pro Tyr Arg Ser
    290                 295                 300

Glu Thr Val Tyr Ser Arg Leu Tyr Glu Gln Cys Arg Pro Asp Pro Ala
305                 310                 315                 320

Gly Arg Trp Pro His Glu Cys Glu Gly Ala Ala Tyr Ala Ala Pro Val
                325                 330                 335

Ala His Leu Arg Pro Ala Asn Asn Ser Val Asp Leu Val Phe Asp Asp
            340                 345                 350

Ala Pro Ala Ala Ala Ser Gly Leu Tyr Val Phe Val Leu Gln Tyr Asn
        355                 360                 365

Gly His Val Glu Ala Trp Asp Tyr Ser Leu Val Val Thr Ser Asp Arg
    370                 375                 380

Leu Val Arg Ala Val Thr Asp His Thr Arg Pro Glu Ala Ala Ala Ala
385                 390                 395                 400

Asp Ala Pro Glu Pro Gly Pro Pro Leu Thr Ser Glu Pro Ala Gly Ala
```

-continued

```
                405                 410                 415

Pro Thr Gly Pro Ala Pro Trp Leu Val Val Leu Val Gly Ala Leu Gly
            420                 425                 430

Leu Ala Gly Leu Val Gly Ile Ala Ala Leu Ala Val Arg Val Cys Ala
        435                 440                 445

Arg Arg Ala Ser Gln Lys Arg Thr Tyr Asp Ile Leu Asn Pro Phe Gly
    450                 455                 460

Pro Val Tyr Thr Ser Leu Pro Thr Asn Glu Pro Leu Asp Val Val Val
465                 470                 475                 480

Pro Val Ser Asp Asp Glu Phe Ser Leu Asp Glu Asp Ser Phe Ala Asp
                485                 490                 495

Asp Asp Ser Asp Asp Asp Gly Pro Ala Ser Asn Pro Pro Ala Asp Ala
            500                 505                 510

Tyr Asp Leu Ala Gly Ala Pro Glu Pro Thr Ser Gly Phe Ala Arg Ala
        515                 520                 525

Pro Ala Asn Gly Thr Arg Ser Ser Arg Ser Gly Phe Lys Val Trp Phe
    530                 535                 540

Arg Asp Pro Pro Glu Asp Asp Ala Ala Pro Ala Arg Ala Pro Ala Ala
545                 550                 555                 560

Pro Asp Tyr Thr Val Val Ala Ala Arg Leu Lys Ser Ile Leu Arg
                565                 570                 575
```

(2) INFORMATION FOR SEQ ID NO: 4:

(i) SEQUENCE CHARACTERISTICS:
(A) LENGTH: 158 amino acids
(B) TYPE: amino acid
(D) TOPOLOGY: linear (ii) MOLECULE TYPE: protein (xi) SEQUENCE DESCRIPTION: SEQ ID NO: 4:

```
Met Glu Arg Ser His Lys Ala Ser Cys Gly Cys Phe Glu Gly Met Glu
  1               5                  10                  15

Ser Pro Arg Ser Val Val Asn Glu Asn Tyr Arg Gly Ala Asp Glu Ala
             20                  25                  30

Asp Ala Ala Pro Pro Ser Pro Pro Pro Glu Gly Ser Ile Val Ser Ile
         35                  40                  45

Pro Ile Leu Glu Leu Thr Ile Glu Asp Ala Pro Ala Ser Ala Glu Ala
     50                  55                  60

Thr Gly Thr Ala Ala Ala Ala Pro Ala Gly Arg Thr Pro Asp Ala Asn
 65                  70                  75                  80

Ala Ala Pro Gly Gly Tyr Val Pro Val Pro Ala Ala Asp Ala Asp Cys
                 85                  90                  95

Tyr Tyr Ser Glu Ser Asp Ser Glu Thr Ala Gly Glu Phe Leu Ile Arg
            100                 105                 110

Met Gly Arg Gln Gln Arg Arg Arg His Arg Arg Arg Arg Cys Met Ile
        115                 120                 125

Ala Ala Ala Leu Thr Cys Ile Gly Leu Gly Ala Cys Ala Ala Ala Ala
    130                 135                 140

Ala Ala Gly Ala Val Leu Ala Leu Glu Val Val Pro Arg Pro
145                 150                 155
```

(2) INFORMATION FOR SEQ ID NO: 5:

(i) SEQUENCE CHARACTERISTICS:
(A) LENGTH: 25 base pairs

-continued

```
         (B) TYPE: nucleic acid
         (C) STRANDEDNESS: single
         (D) TOPOLOGY: linear

    (ii) MOLECULE TYPE: DNA (genomic)

   (iii) HYPOTHETICAL: NO

   (iii) ANTI-SENSE: NO

    (xi) SEQUENCE DESCRIPTION: SEQ ID NO: 5:

GGCATTTGGA TCCAATGCAA CCCAC                                           25


(2) INFORMATION FOR SEQ ID NO:6:

     (i) SEQUENCE CHARACTERISTICS:
         (A) LENGTH: 39 base pairs
         (B) TYPE: nucleic acid
         (C) STRANDEDNESS: double
         (D) TOPOLOGY: linear

    (ii) MOLECULE TYPE: DNA (genomic)

   (iii) HYPOTHETICAL: NO

    (iv) ANTI-SENSE: NO

    (xi) SEQUENCE DESCRIPTION: SEQ ID NO:6:

GGGAGTCCCG GAGTCCCGGC CCCCAGAGCC CCGTTCGAA                            39


(2) INFORMATION FOR SEQ ID NO:7:

     (i) SEQUENCE CHARACTERISTICS:
         (A) LENGTH: 39 base pairs
         (B) TYPE: nucleic acid
         (C) STRANDEDNESS: double
         (D) TOPOLOGY: linear

    (ii) MOLECULE TYPE: DNA (genomic)

   (iii) HYPOTHETICAL: NO

    (iv) ANTI-SENSE: NO

    (xi) SEQUENCE DESCRIPTION: SEQ ID NO:7:

GCCGTCCTGG CGTTGGAGGT AGTGCCCCGG CCCTGAGGG                            39
```